US00RE40488E

(19) United States
(12) Reissued Patent
Nagata et al.

(10) Patent Number: US RE40,488 E
(45) Date of Reissued Patent: Sep. 9, 2008

(54) ORIENTATION MEASURING INSTRUMENT

(75) Inventors: Shinichi Nagata, Amagasaki (JP); Seiichi Miyamoto, Amagasaki (JP); Fumiaki Okada, Kamakura (JP)

(73) Assignee: Oji Paper Co., Ltd., Tokyo-to (JP)

(21) Appl. No.: 10/740,393

(22) PCT Filed: Mar. 25, 1998

(86) PCT No.: PCT/JP98/01356

§ 371 (c)(1),
(2), (4) Date: Sep. 8, 1999

(87) PCT Pub. No.: WO98/44340

PCT Pub. Date: Oct. 8, 1998

Related U.S. Patent Documents

Reissue of:
(64) Patent No.: 6,396,288
Issued: May 28, 2002
Appl. No.: 09/380,583
Filed: Sep. 8, 1999

(30) Foreign Application Priority Data

Mar. 28, 1997 (JP) ..... 9-095135
Sep. 8, 1997 (JP) ..... 9-260984

(51) Int. Cl.
*H01P 3/16* (2006.01)
*G01N 22/00* (2006.01)

(52) U.S. Cl. ..... 324/631; 324/633; 324/637
(58) Field of Classification Search ..... 324/631, 324/636, 633, 637
See application file for complete search history.

(56) References Cited

U.S. PATENT DOCUMENTS 4,500,385 A * 2/1985 Heikkla ..... 324/631
4,710,700 A * 12/1987 Osaki et al. ..... 324/631
4,841,223 A * 6/1989 Baum et al. ..... 324/631
4,868,488 A * 9/1989 Schmall ..... 324/635

(Continued)

FOREIGN PATENT DOCUMENTS

| | | | |
|---|---|---|---|
| EP | 547968 A1 | * | 6/1993 |
| EP | 0 547 968 A1 | | 6/1993 |
| EP | 0 710 917 | | 4/1995 |
| JP | 1-163645 | * | 6/1989 |
| JP | 1-270648 | * | 10/1989 |
| JP | 2-29982 | * | 7/1990 |
| JP | 3-39632 | * | 6/1991 |
| JP | 3-70368 | * | 7/1991 |
| JP | 4-9467 | * | 2/1992 |
| JP | 7-14870 | * | 4/1995 |
| JP | 07-120515 A | | 5/1995 |
| JP | 7-225200 | * | 8/1995 |
| JP | 7-270342 | * | 10/1995 |
| JP | 8-122375 | * | 5/1996 |
| JP | 8-271449 | * | 10/1996 |
| WO | WO-96/11410 A1 | | 4/1996 |
| WO | WO 9701088 A1 | * | 1/1997 |
| WO | WO 97/01088 | | 1/1997 |

OTHER PUBLICATIONS

European Search Report dated Jan. 2, 2003.
Japanese Office Action mailed Mar. 22, 2005 (3 pages).
International Search Report, Feb. 14, 2000.*

*Primary Examiner*—Anjan Deb
(74) *Attorney, Agent, or Firm*—Brian K. Dutton; Rader Fishman & Grauer PLLC

(57) ABSTRACT

It is possible to generate a resonance mode such that a dielectric resonator (20) can be resonated and an electric field vector leaking out from the resonator (20) exists by arranging antennas (22a and 22b) for the resonator (20). When a sample [(22)] (*25*) has dielectric anisotropy, the resonance frequency of the resonator (20) varies when the sample (25) or resonator (20) is rotated. The dielectric anisotropy of the sample (25) is found from the variance of the resonance frequency. Thus the dielectric anisotropy of not only a sheet-like sample, but also such a sample as a three-dimensional molded sample can be measured.

7 Claims, 27 Drawing Sheets

U.S. PATENT DOCUMENTS 4,904,928 A 2/1990 Lewis
5,119,034 A * 6/1992 Ishikawa et al. ..... 324/633
5,334,941 A * 8/1994 King ..... 324/637
5,506,497 A * 4/1996 Klein et al. ..... 324/71.6
5,532,604 A 7/1996 Nagata
5,563,505 A * 10/1996 Dorothy et al. ..... 324/71.6
5,699,163 A * 12/1997 Todoroki et al. ..... 356/445
6,049,211 A * 4/2000 Varpula et al. ..... 324/636
6,375,875 B1 * 4/2002 Paulauskas et al. ..... 264/29.2
6,496,018 B1 * 12/2002 Nagata et al. ..... 324/636
6,538,454 B1 * 3/2003 Frenkel et al. ..... 324/637

* cited by examiner

| MODE | a | 15mm | | 15mm | | 15mm | |
|---|---|---|---|---|---|---|---|
| | b | 19 | | 30 | | 16.5 | |
| | l | 19 | B | 16.5 | E | 11 | D |
| | | CALCULATED VALUE | MEASURED VALUE | CALCULATED VALUE | MEASURED VALUE | CALCULATED VALUE | MEASURED VALUE |
| 101 |  | 1.791 GHz | 2.2 GHz | 1.834 | 2.1 | 2.022 | 2.5 |
| 102 |  | 2.555 | 2.833 | 2.783 | 3.061 | 3.724 | 4.248 |
| 201 |  | 3.397 | | 3.425 | | 3.557 | |
| 103 |  | 3.625 | | 4.063 | | >6.0 | |
| 202 |  | 3.865 | | 4.028 | | 4.756 | |

EXCITATION BY ROD ANTENNA

EXCITATION BY LOOP ANTENNA

CAVITY RESONATOR

ELECTRIC FIELD DISTRIBUTION BY ROD ANTENNA

CIRCULAR DIELECTRIC RESONATOR

ELECTRIC FIELD DISTRIBUTION BY LOOP ANTENNA

SQUARE DIELECTRIC RESONATOR

ELECTRIC FIELD DISTRIBUTION BY LOOP ANTENNA

SQUARE DIELECTRIC RESONATOR

ELECTRIC FIELD DISTRIBUTION BY ROD ANTENNA

FREQUENCY SHIFT → 0.6MHz

ORIENTATION MEASURING INSTRUMENT

Matter enclosed in heavy brackets [ ] appears in the original patent but forms no part of this reissue specification; matter printed in italics indicates the additions made by reissue.

TECHNICAL FIELD

The present invention relates to an instrument measuring the orientation of those inclusive of sheet-like substances such as a polymer sheet including a film and paper and stereoscopic articles such as moldings of plastic, resin, rubber and the like with a microwave.

BACKGROUND TECHNIQUE

The fiber orientation of paper corresponds to the chain direction of molecules forming fiber, and is closely related with curling, torsion, inclination of NIP (Non-Impact Printer) paper and the like. Standards in fiber orientation are becoming strict particularly in these several years, and several types of measuring methods have been employed. There are a water diffusion method, a dynamic rupture intensity method, an ultrasonic method, a microwave method and the like as such measuring methods, and the correspondence between operations on a wire part and the orientation is substantially being elucidated at present.

On the other hand, in the case of a polymer film, that forming the film is not fiber, and anisotropy of the arrangement of molecular chains can be grasped as the anisotropy of various physical properties, for example, optical, electrical and mechanical intensity and the like. Therefore, inclusive of paper, polymer film and the like, the orientation can be collectively grasped as the anisotropy (molecular orientation) of the arrangement of molecular chains.

It is general that a solid polymer has orientation in the process where molecular chains are solidified from a fluidized state due to the shape thereof. Due to the orientation, anisotropy appears in a dynamic, thermal, optical or electromagnetic physical property. Consequently, for example, anisotropy of the modulus of elasticity, anisotropy of the ratio of heat contraction or the like, takes place to cause various problems in quality.

As methods of measuring such anisotropy, an X-ray diffraction method, an infrared polarization method, a fluorescence polarization method, a birefringence method, an ultrasonic method, a microwave method and the like are employed.

Among these methods, the X-ray diffraction method and the fluorescence polarization method require time and labor for measurement, while measurement is difficult in relation to a thick sample in the infrared polarization method. The birefringence method is a method of optically measuring anisotropy by utilizing a refraction phenomenon based on anisotropy of a refraction index, and an opaque sample cannot be measured since transparency with respect to visible light or near infrared light is required for measurement. The ultrasonic method is of a contact type and hence unsuitable for a moving sample.

A method employing resonance of a microwave utilizes anisotropy of a dielectric constant The dielectric constant has a constant relation also with a refractive index. The method employing a microwave is utilized for molecular orientation measurement regardless of presence/absence of optical transparency inclusive of paper and a polymer film.

FIG. 1 illustrates the principle of a conventional orientation meter employing a microwave cavity resonator. It comprises a microwave introduction part 2 on one end portion and a microwave detection part 4 on another end portion. The part between these end portions defines a microwave resonator 6 formed by a waveguide having a constant electric field vibrational direction. The resonator 6 is provided with a slit 8 in a direction perpendicularly crossing the axis of the resonator 6 on the position of a loop part of a standing wave. A sample 10 is arranged in the slit 8, a microwave is introduced from the microwave introduction part 2, and the microwave intensity is detected with the microwave detection part 4. The sample 10 is rotated around the axis of the resonator 6, and the intensity of the transmitted microwave is detected every rotational angle for obtaining the orientation pattern. It is also possible to obtain a dielectric constant pattern by obtaining the dielectric constant every rotational angle position from deviation between the resonance frequency when arranging the sample 10 in the slit 10 and the resonance frequency when arranging no sample.

As a method of measuring the dielectric constant with a microwave, that shown in FIG. 2 is proposed (refer to Japanese Utility Model Laying-Open Gazette Jitsu Kai Hei 3-70368). There, it comprises a pair of dielectric resonators 12a and 12b opposite to each other through a sample 10. A pair of terminals 14a and 14b oppositely arranged through the dielectric resonator 12a are provided on side portions of one dielectric resonator 12a. An electric field vector having one direction parallel to the plane of the sample 10 is generated in the dielectric resonators 12a and 12b by these terminals 14a and 14b, for measuring the dielectric constant from the resonance characteristics thereof. Here, the terminals 14a and 14b are loop-like. It is also possible to comprise a plurality of pairs of terminals 14a and 14b and measure dielectric anisotropy of the sample by switching operations thereof.

In the measuring instrument shown in FIG. 1 or FIG. 2, cavity resonators or dielectric resonators are oppositely arranged on both sides through the sample 10, and hence the shape of the measured sample 10 is limited to a sheet-like one.

Accordingly, a first object of the present invention is to make it possible to measure dielectric anisotropy not only in a sheet-like sample but also in a sample such as a stereoscopic molding.

An electric field vector in an in-sample plane required is desirably more uniform during measuring the dielectric anisotropy.

While the terminals 14a and 14b are loop-like in the measuring instrument shown in FIG. 2, a second object of the present invention is to find a terminal shape which can further attain uniformity of an electric field vector than the loop-like terminal and improve sensitivity of dielectric anisotropy measurement.

DISCLOSURE OF THE INVENTION

One aspect of the present invention comprises a dielectric resonator having a plane being close to or being in contact with a sample, a microwave exciter generating an electric field vector having a unidirectional component at a frequency in the vicinity of the resonance frequency of the dielectric resonator when the sample is present and in an in-sample plane parallel to the said plane in the dielectric resonator, a detector detecting transmission energy or reflection energy by the dielectric resonator, a rotation mechanism rotating the sample or the dielectric resonator in a plane parallel to the said plane, and a data processor obtaining dielectric anisotropy of the sample from variance of a detection output of the detector following rotation by the rotation mechanism.

This aspect is suitable for obtaining the dielectric anisotropy of a specific part of the sample.

Another aspect of the present invention comprises a plurality of dielectric resonators comprising planes being close to or being in contact with a sample and arranged close to each other, a microwave exciter generating electric field vectors having unidirectional components, which are electric field vectors having directions different from each other at a frequency in the vicinity of the resonance frequency of the dielectric resonators when the sample is present and in an in-sample plane parallel to the said planes in the respective dielectric resonators, detectors for the respective dielectric resonators detecting transmission energy or reflection energy by these dielectric resonators, and a data processor obtaining dielectric anisotropy of the sample from variance of detection outputs by the detectors at the electric field vectors of different directions from the plurality of dielectric resonators.

According to this aspect, neither the sample nor the dielectric resonators may be rotated but the dielectric anisotropy of the sample can be obtained by outputs from the plurality of dielectric resonators, whereby it is suitable for continuously measuring a sample flowing online.

Still another aspect of the present invention comprises a dielectric resonator having a plane being close to or being in contact with a sample, a plurality of sets, which are sets of microwave exciters generating electric field vectors having unidirectional components at a frequency in the vicinity of the resonance frequency of the dielectric resonator when the sample is present and in an in-sample plane parallel to the said plane in the dielectric resonator and detectors detecting transmission energy or reflection energy by the dielectric resonator, arranged on positions different from each other with respect to the dielectric resonator, a switching driver selecting one set among the plurality of sets of microwave exciters and detectors and sequentially driving the same, and a data processor obtaining dielectric anisotropy of the sample from variance of detection outputs of the detectors following switching by the switching driver.

According to this aspect, neither the sample nor the dielectric resonator may be rotated but the dielectric anisotropy of the sample can be obtained by switching operations of the sets of the microwave exciters and the detectors by the switching driver, whereby it is suitable for continuously measuring a sample flowing online also in this case.

Variance of the detection output by the detector can be measured as variance of the resonance frequency. The variance of the resonance frequency can be measured as the shift quantity of the frequency itself. The variance of the detection output by the detector can also be detected as variance of detection energy at a specific frequency.

Terminals of the microwave exciter and the detector can be rendered loop-like, or can be rendered rod-like terminals. When loop-like, coupling occurs through magnetic field, and when rod-like, coupling occurs through electric field. Electric field distribution on the position of the sample is decided by a resonance mode determined by the shape, the magnitude, an excitation method, the dielectric constant etc. of the dielectric resonator, and hence it is desirable to select such a resonance mode that an electric field as parallel as possible to the plane being close to or being in contact with the sample is produced.

The loop-like or rod-like terminals may be so arranged that the directions of magnetic field distribution or electric field distribution in the resonance mode to be resonated and the magnetic field or the electric field produced by the loop-like or rod-like terminals vectorially coincide with each other, and are preferably arranged in the vicinity of or inside the dielectric resonator. For example, rod-like terminals can be arranged in a direction perpendicular or parallel to the plane of the dielectric resonator being close to or being in contact with the sample.

When detecting transmission energy with the detector, the exciter and the detector are connected respectively to a pair of loop-like or rod-like terminals oppositely arranged through the dielectric resonator.

Furthermore, when detecting reflection energy with the detector, the exciter and the detector are connected to one common loop-like or rod-like terminal arranged close to the dielectric resonator.

The dielectric resonator is a cylindrical resonator or a square resonator.

The periphery of the dielectric resonator is preferably covered with a shielding material consisting of a conductive material except a sample measuring surface. Thus, the Q value of a resonance curve can be increased. At this time, it is preferable that a shielding material consisting of a conductive material is arranged also above a sample measuring surface of the dielectric resonator so that the sample is arranged between the sample measuring surface of the dielectric resonator and the shielding material above the sample measuring surface.

FIG. 3(A) schematically shows one embodiment With respect to a dielectric resonator 20, proper microwave loop antennas (or rod antennas) 22a and 22b are arranged on proper positions in proper directions with respect to the dielectric resonator 20. It is possible to produce a resonance mode resonating the dielectric resonator 20, where an electric field vector leaking outward from the resonator 20 is present, by the antennas 22a and 22b. For resonance modes, there is a TM mode or a TE mode when the dielectric resonator 20 is square, and there is an HEM mode or the like when it is cylindrical. The intensity of an electric field vector 24 substantially exponentially decreases as separating from the dielectric resonator 20, while the resonance frequency shifts by electromagnetic coupling in response to the dielectric constant of a sample by placing the sample 25 in separation from the dielectric resonator 20 by a small distance or in contact with the dielectric resonator 20.

FIG. 3(A) schematically shows the structure in the case of employing a cylindrical dielectric resonator as the dielectric resonator 20 and making an $HEM_{11\delta}$ mode, while a microwave going out from an oscillator 26 generates an electric field through the loop antenna 22a, and the dielectric resonator 20 resonates by electromagnetic coupling. The resonance frequency in this case is decided by the dimensions and the dielectric constant of the dielectric resonator 20. Assuming that the radius of the cylinder of the dielectric resonator 20 is a, the length is L and the dielectric constant is $\in$, the resonance frequency f (GHz) is approximately obtained as:

$$f=34(a/L+3.45)/a/\in^{1/2}$$

FIG. 3(B) expresses FIG. 3(A) as an equivalent circuit. With respect to the resonance frequency when placing no sample, the resonance frequency shifts by the capacitance Cr changing in response to the dielectric constant of the sample 25 when placing the sample 25. When the dielectric constant of the sample 25 has anisotropy, the resonance frequency also shifts with depending on the directions of the sample 25 and the electric field vector 24.

FIG. 4 shows electric field distribution in the $HEM_{11\delta}$ mode. (A) shows electric field distribution on a horizontal plane around an end of the dielectric resonator 20, and (B) shows electric field distribution on a meridian section plane of $\phi=0$ ($\phi$: angle from a reference direction in the horizontal plane).

Returning to FIG. 3 and making description, the microwave going out from the oscillator 26 is magnetically coupled with the dielectric resonator 20 by the loop antenna 22a, and the dielectric resonator 20 can enter a resonant state. The electric field vector of the dielectric resonator 20 appears in the form substantially parallel to the plane of the sample 25, and interaction with a dipole moment provided in the sample 25 takes place. Here, with rotating the sample 25 or the dielectric resonator 20 in parallel planes of the sample 25 and the dielectric resonator 20 by detecting microwave intensity appearing in a detector 28 in correspondence to its rotational angle, the orientation state can be obtained from angle dependency of the intensity. A controller 30 controls the frequency of the microwave generated from the oscillator 26 and captures the microwave intensity by the detector 28, 32 is a computer as a data processor obtaining the orientation state from the angle dependency of the detected microwave intensity.

The principle of orientation measurement is further described. In the dielectric resonator 20, there is relation shown in FIG. 5(A) between the intensity of the transmitted microwave and the frequency. This resonance curve is referred to as a Q curve. With the sample 25 being placed, the Q curve varies by the following relation:

$$\frac{\omega-\omega_0}{\omega_0}=\frac{1}{4W}\int_{\Delta v}\left[\left(P+\frac{j}{j\omega}\right)\cdot E_0^{-}+\mu_0 M\cdot H_0^{+}\right]dv$$

$$\overline{W}=\frac{1}{2}\int_{\Delta v}\varepsilon_0|E_0|^2 dv$$

$\omega=2\pi f$ $\omega$: complex angular frequency (sample)

$\omega_a$: complex angular frequency (blank)

P: electric polarization

J: conductive current density $E_a$: electric field

M: magnetic field $H_a$: magnetization

*: indicates that it is a complex number

That showing the variance is FIG. 5(B). When the sample 25 has anisotropy in a plane opposite to the dielectric resonator 20 and if the sample 25 or the dielectric resonator 20 is rotated in a plane parallel to the plane, the peak frequency (resonance frequency) of the Q curve varies every relative rotational angle position (S) of the sample 25 with respect to the dielectric resonator 20 as shown in FIG. 6(A), for example. In this rotation, in a Q curve shifting to the highest frequency side, for example, it is assumed that detected intensity of the transmitted microwave at the frequency is 1 and such a frequency that detected intensity on the high frequency side is 1/2 is $f_1$. The detected intensity of the transmitted microwave at each rotational angle at the frequency $f_1$ is shown as a section of FIG. 6(B). Rewriting it with the rotational angle S on the horizontal axis, it becomes as shown in FIG. 7(A). Further rewriting it in a spherical coordinate system, it becomes elliptic as shown in FIG. 7(B), and the orientation angle ($\phi$) and the degree of orientation (a/b) can be obtained from this result, a is the major axis length of the elliptic, and b is the minor axis length.

The present invention comprises a dielectric resonator having a plane being close to or being in contact with a sample, and rotates the sample or the dielectric resonator in the plane or changes the direction of an electric field vector while generating the electric field vector having a unidirectional component at a frequency in the vicinity of the resonance frequency of the dielectric resonator when the sample is present and in an in-sample plane parallel to the plane. Alternatively, it comprises a plurality of dielectric resonators having planes being close to or being in contact with a sample and arranged close to each other, and generates electric field vectors having unidirectional components which are electric field vectors having directions different from each other at a frequency in the vicinity of the resonance frequency of the dielectric resonators when the sample is present and in an in-sample planes parallel to the planes in the respective dielectric resonators. Then, it obtains dielectric anisotropy of the sample from variance of a detection value of resonance energy following rotation of the sample or the dielectric resonators or change of the electric field vectors or detection values of resonance energy from the plurality of dielectric resonators having different directions of electric field vectors. Thus, it is possible to measure dielectric anisotropy not only in the case where the shape of the sample is a sheet-like one but also in a sample such as a stereoscopic molding.

A moving sample can be continuously measured by rotating the dielectric resonator, changing the direction of the electric field vector or arranging a plurality of dielectric resonators having different directions of electric field vectors, so that it is applicable to online measurement on the production site.

Also, when the dielectric resonator is covered with a conductive shielding member except a part where the sample is arranged, Q of a resonance spectrum increases and measurement with a considerate S/N ratio is enabled.

BEST MODES FOR CARRYING OUT THE INVENTION

Figure 8:
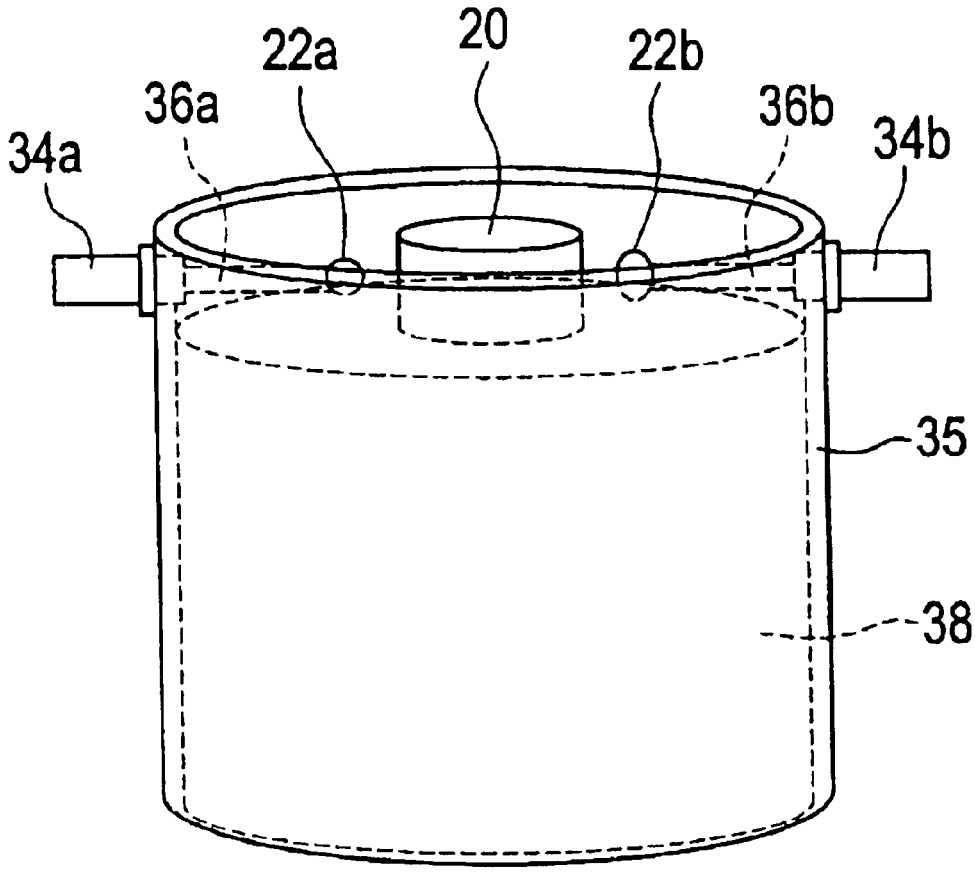
FIG. 8 is a perspective view showing a first embodiment.

FIG. 8 shows a first embodiment A discharge polyethylene molding is put as a supporter 38 of a low dielectric constant in a cylindrical shield case 35 of brass whose upper part has an opening, and a cylindrical dielectric resonator 20 is mounted on the supporter 38 with the bottom surface in the horizontal direction. In the dielectric resonator 20, its upper surface is set substantially flush with an edge of the opening of the shield case 35, and a sample is placed on the opening part of the shield case 35. Orientation of the dielectric constant of the sample can be measured by rotating the sample in a horizontal plane in the opening part or rotating the dielectric resonator 20 in a horizontal plane.

Holding the dielectric resonator 20, a pair of loop antennas 22a and 22b are arranged on both sides thereof, and loops thereof are fixed in a perpendicular direction. The loop antennas 22a and 22b are connected with respective connectors 34a and 34b through semi-rigid cables 36a and 36b, and connected to an oscillator and a detector from the connectors 34a and 34b respectively.

Figure 9A:
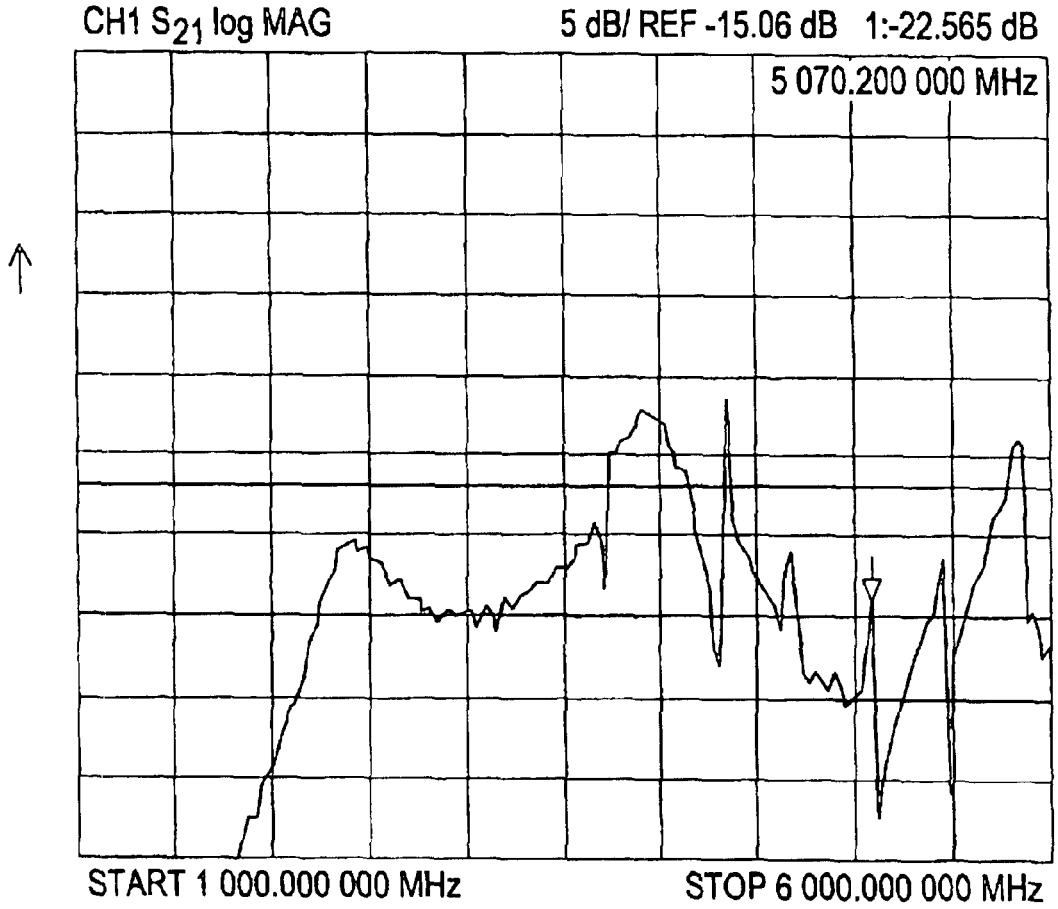
FIG. 9(A) is a diagram showing a transmission energy spectrum when placing no sample in a measurer of the embodiment.
Figure 9B:
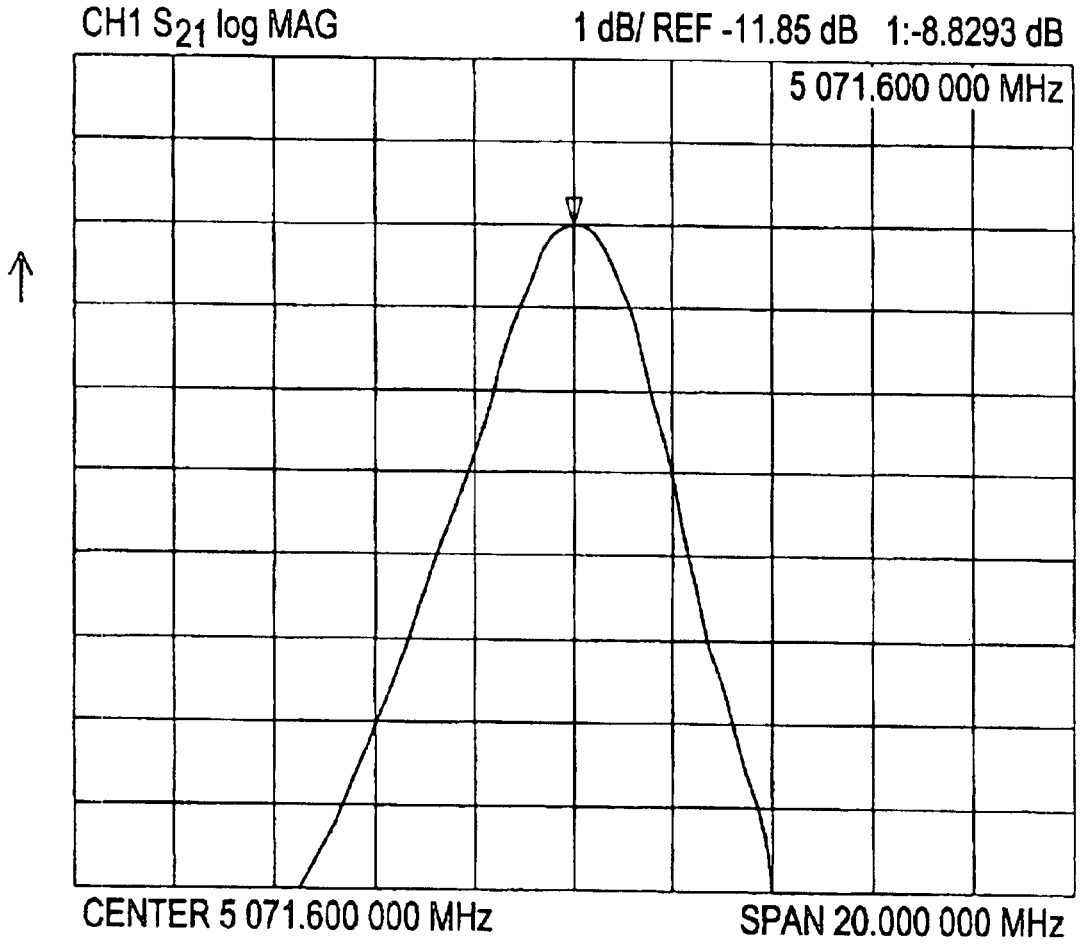
FIG. 9(B) is a diagram enlarging a part shown by arrow in (A).

FIG. 9 shows an example measuring resonance with this measuring instrument while placing no sample. The horizontal axis shows a microwave frequency, and the vertical axis shows transmission energy. (A) shows a transmission energy spectrum when scanning microwave frequencies from 1000 MHz to 6000 MHz, while (B) is an enlargement of the area shown by arrow in (A), expressing a resonating state.

Figure 1:
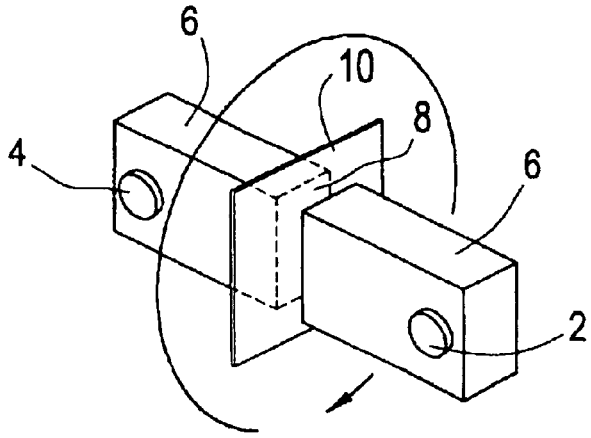
FIG. 1 PRIOR ART
FIG. 1 is a schematic perspective view showing a conventional orientation measuring instrument employing a microwave cavity resonator.
Figure 2:
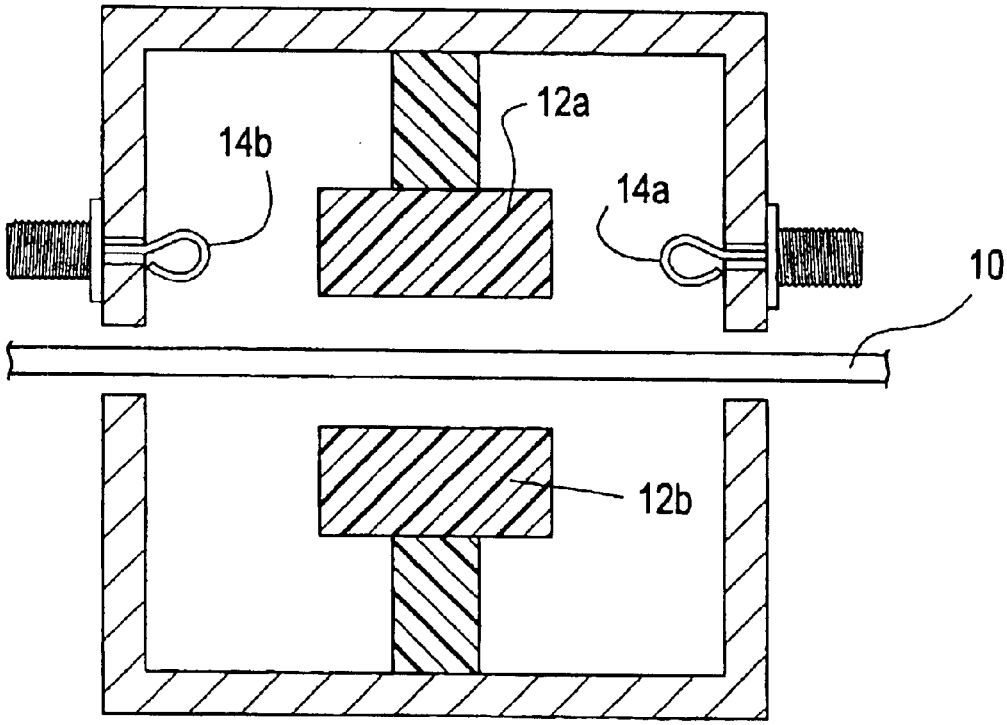
FIG. 2 PRIOR ART
FIG. 2 is a sectional view showing a conventional orientation measuring instrument employing a dielectric resonator.
Figure 3A:
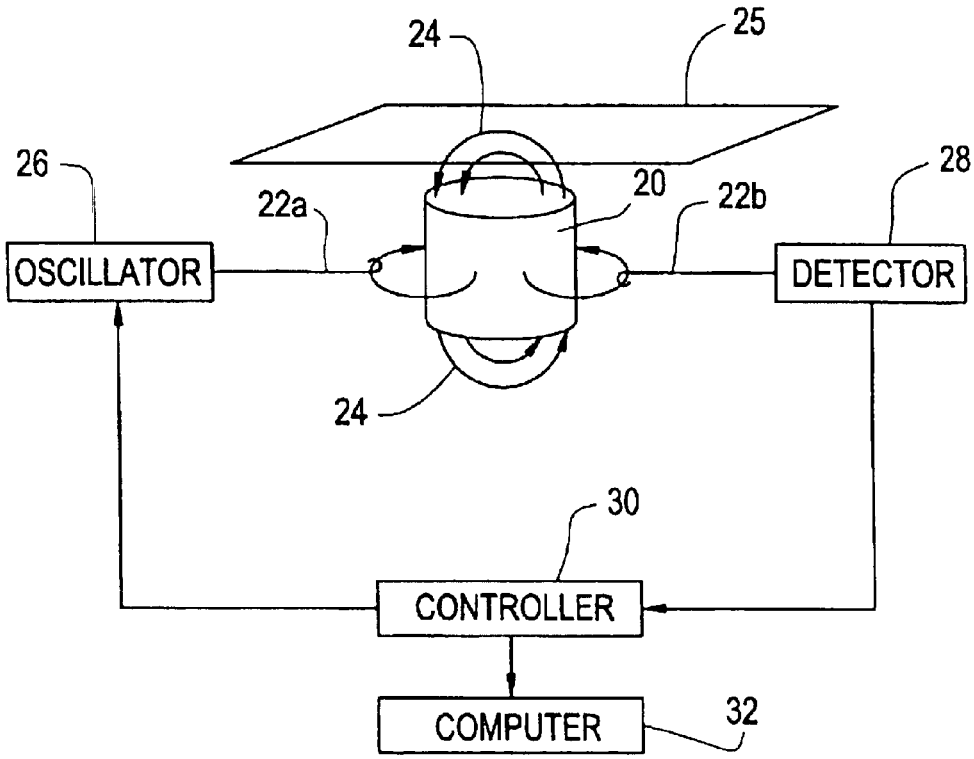
FIG. 3(A) is a schematic perspective view of one embodiment illustrating the principle of the present invention.
Figure 3B:
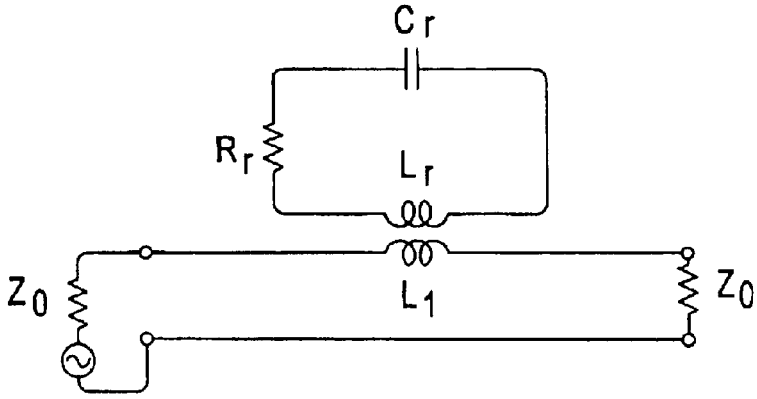
FIG. 3(B) is an equivalent circuit diagram thereof.
Figure 4A:
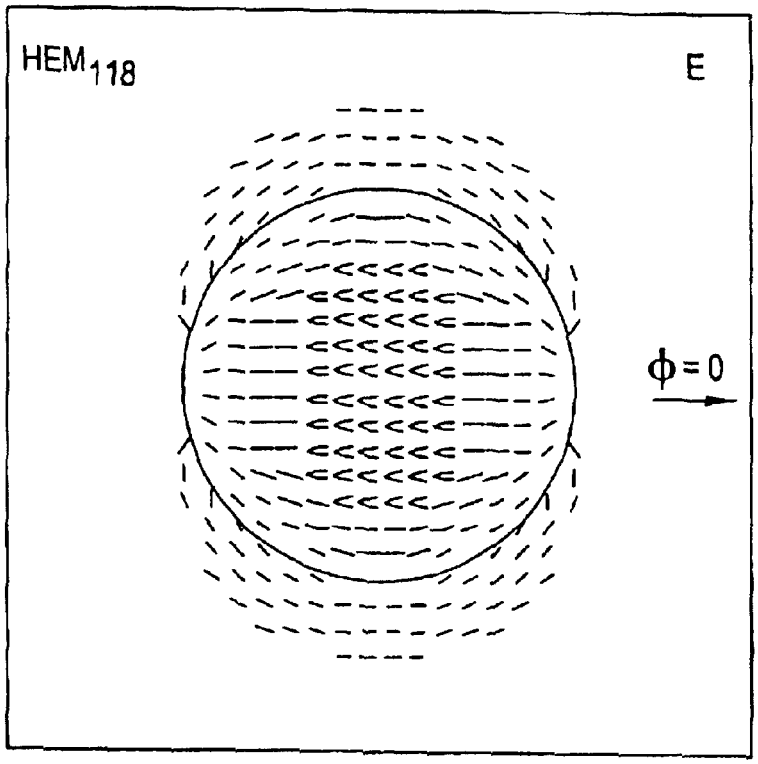
FIG. 4 shows electric field distribution in an $HEM_{11\delta}$ mode in a dielectric resonator, (A) is electric field distribution on a horizontal plane in the vicinity of an end of the dielectric resonator, and (B) is electric field distribution on a meridian section plane of $\phi=0$.
Figure 4B:
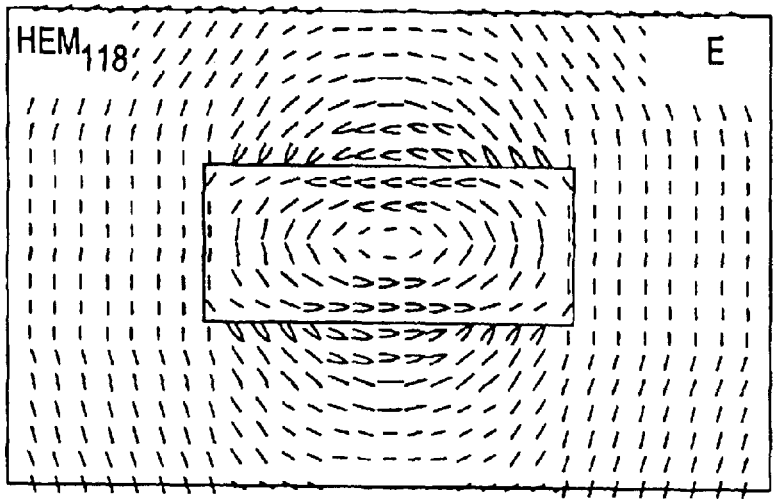
Figure 5A:
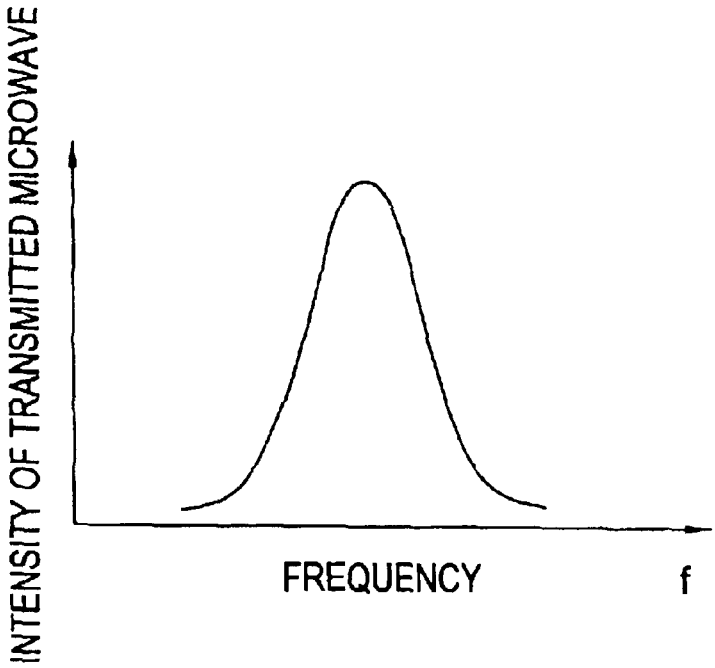
FIG. 5(A) is a diagram of a Q curve showing the relation between the intensity of a transmitted microwave and the frequency in the dielectric resonator.
Figure 5B:
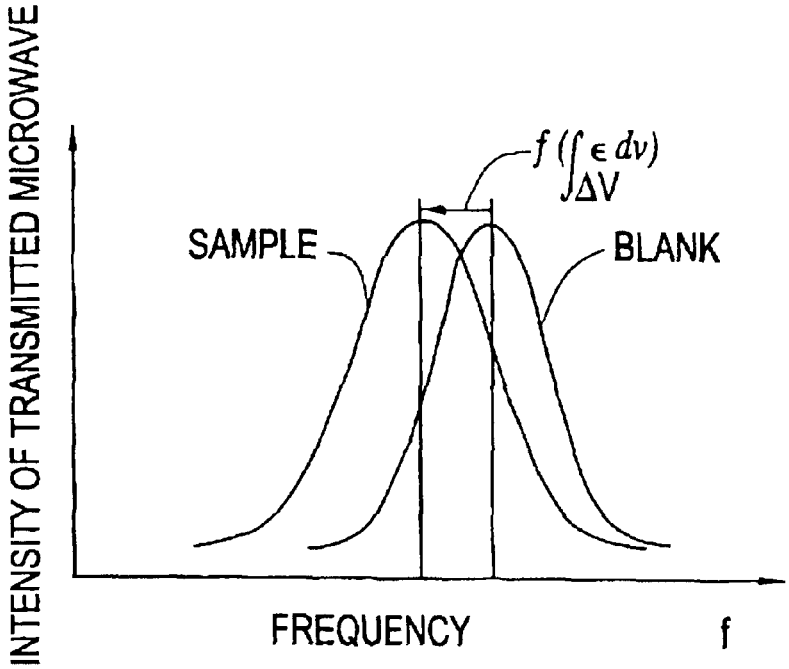
FIG. 5(B) is a diagram showing resonance frequency shift following dielectric constant change.
Figure 6A:
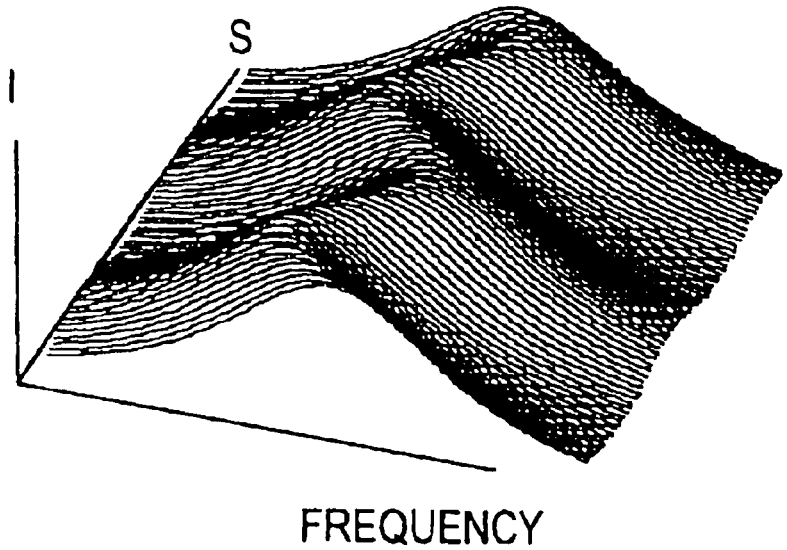
FIG. 6(A) is a diagram showing variance of a Q curve when rotating a sample or a dielectric resonator.
Figure 6B:
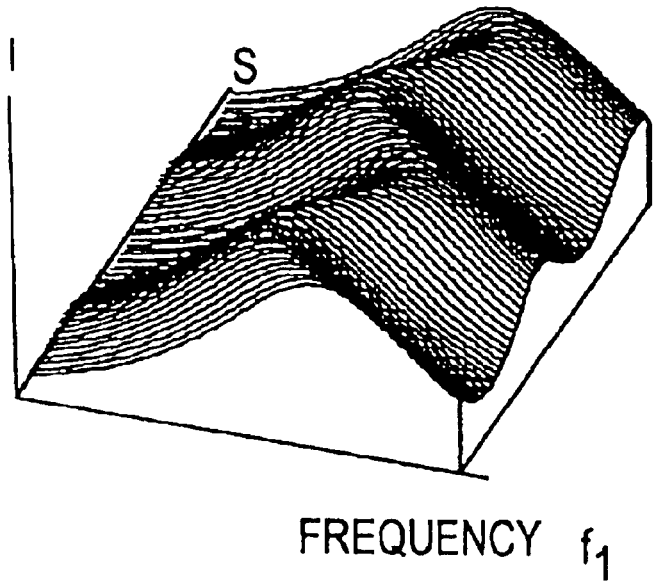
FIG. 6(B) is a diagram showing a section at a specific frequency.
Figure 7A:
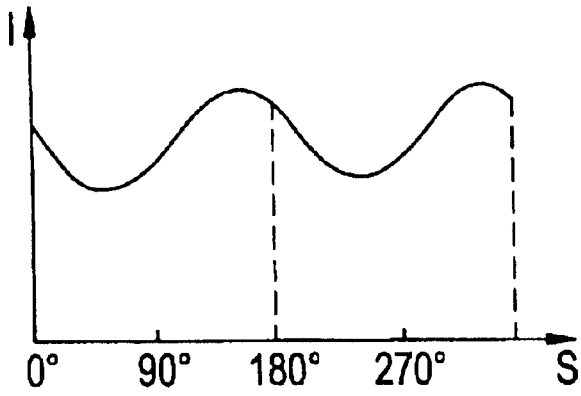
FIG. 7(A) is a diagram rewriting the section of FIG. 6(B) with a rotational angle S on the horizontal axis.
Figure 7B:
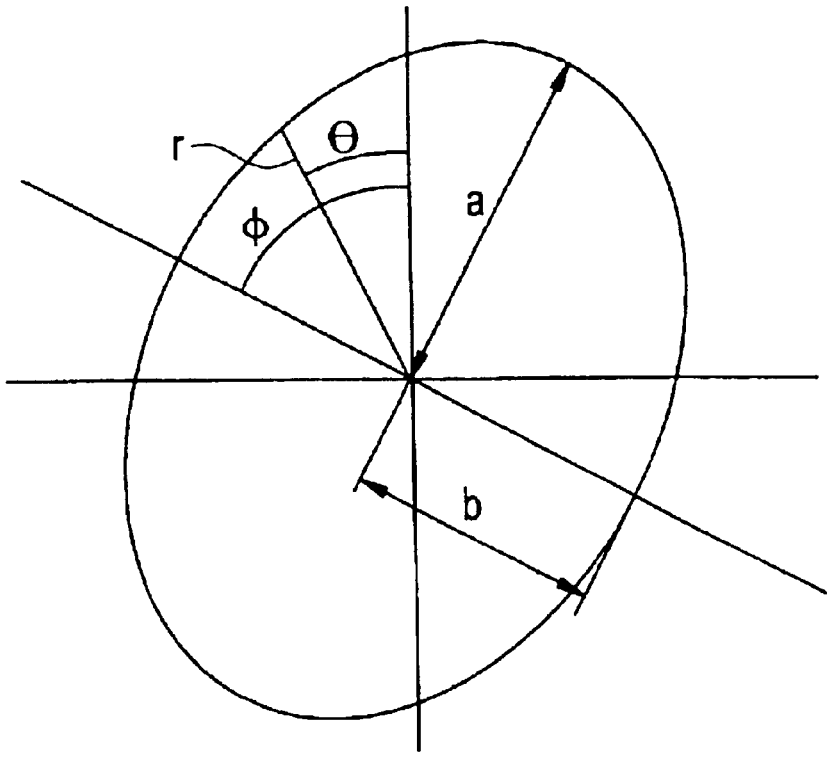
FIG. 7(B) is a diagram further rewriting it in a spherical coordinate system.
Figure 10A:
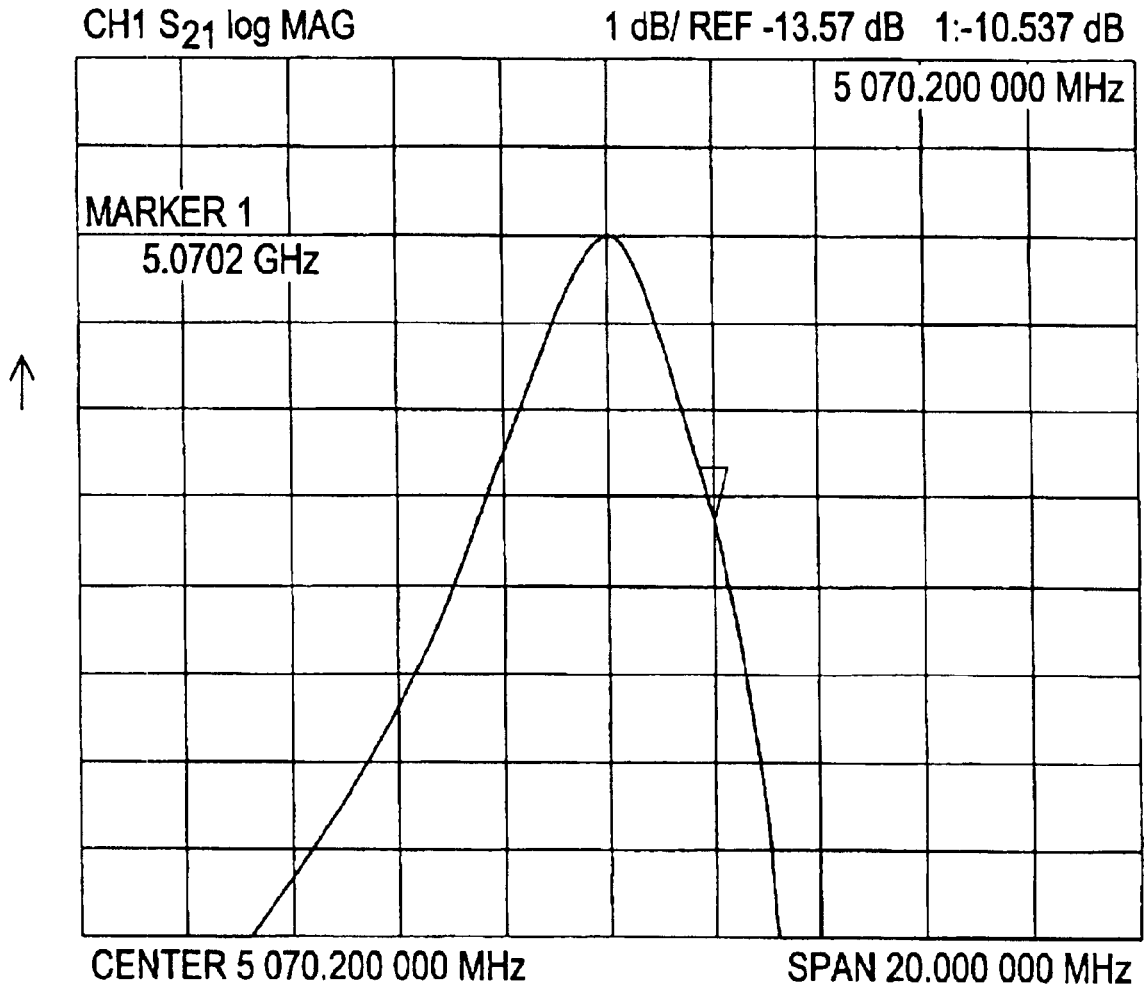
FIG. 10 is a diagram showing a resonance peak around 5070.2 MHz in the embodiment, (A) is at blank measurement placing no sample, and (B) is the case of placing paper as the sample.
Figure 10B:
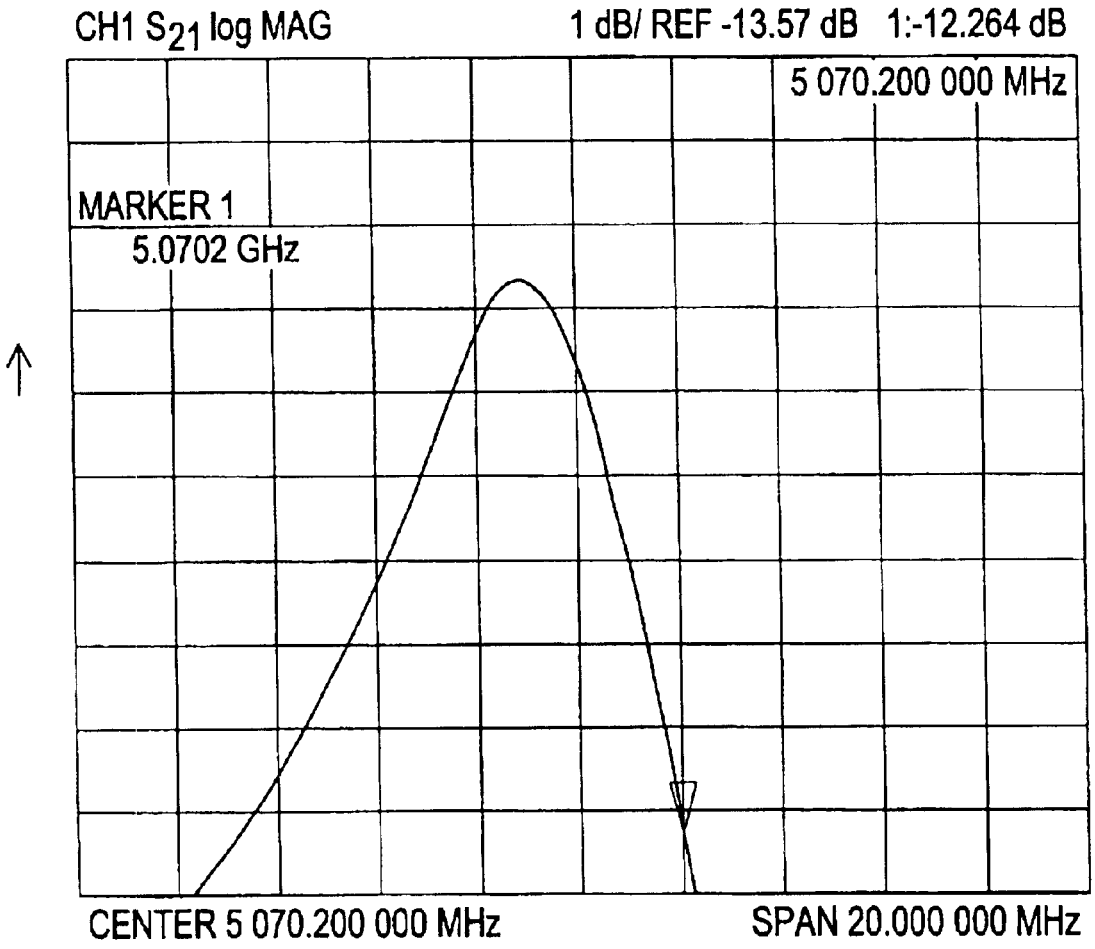

FIG. 10(A) shows a resonance peak at a microwave frequency of 5070.2 MHz when placing no sample (in blank measurement) in the embodiment. On the other hand, FIG. 10(B) shows resonance in the case of placing a sheet of paper on the opening part of the shield case 35 as the sample. It is understood that the peak position shifts to the lower frequency side by placing the sample. When fixing the transmission frequency on the position shown by arrow and making measurement, an output lowers by placing the sample. By rotating the sample or the dielectric resonator 20 in a plane parallel to the plane of the dielectric resonator 20, orientation can be measured as shown from FIG. 5 to FIG. 7 when the sample has anisotropy.

Figure 11A:
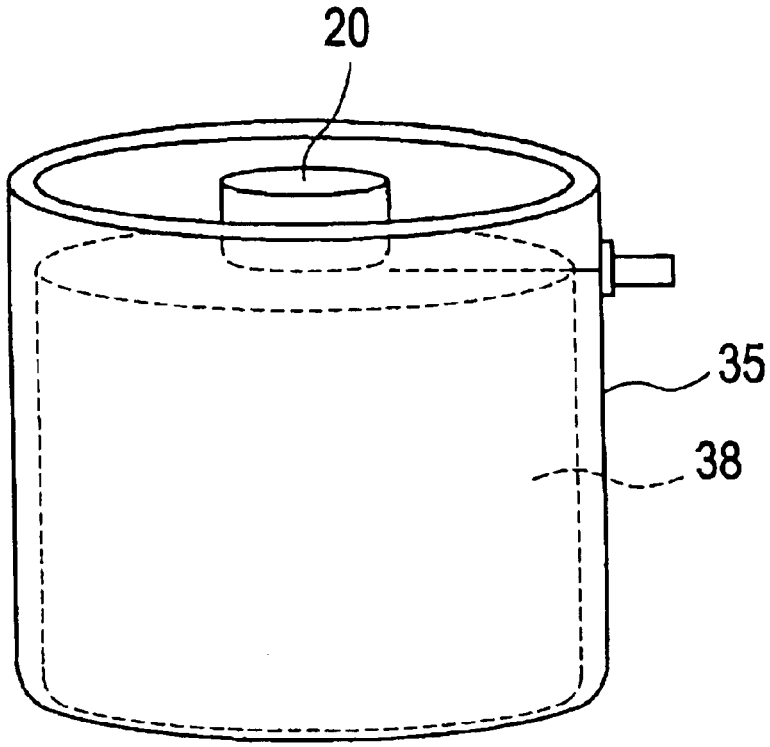
FIG. 11(A) is a perspective view showing an embodiment measuring reflection energy by a dielectric resonator.

FIG. 11(A) shows an embodiment for measuring reflection energy by a dielectric resonator 20, and a rod antenna 40 is arranged on the lower surface side of the dielectric resonator 20 as shown in (B). The rod antenna 40 supplies a microwave from an oscillator to the dielectric resonator 20, while detecting the reflection energy by the dielectric resonator 20.

Figure 11B:
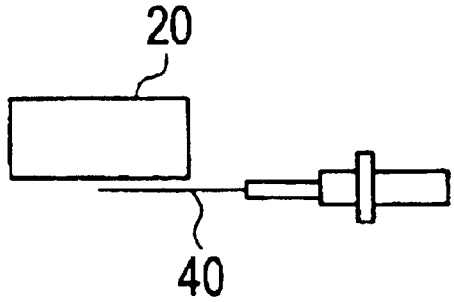
FIG. 11(B) is a front elevational view showing a dielectric resonator and a rod antenna there.
Figure 12A:
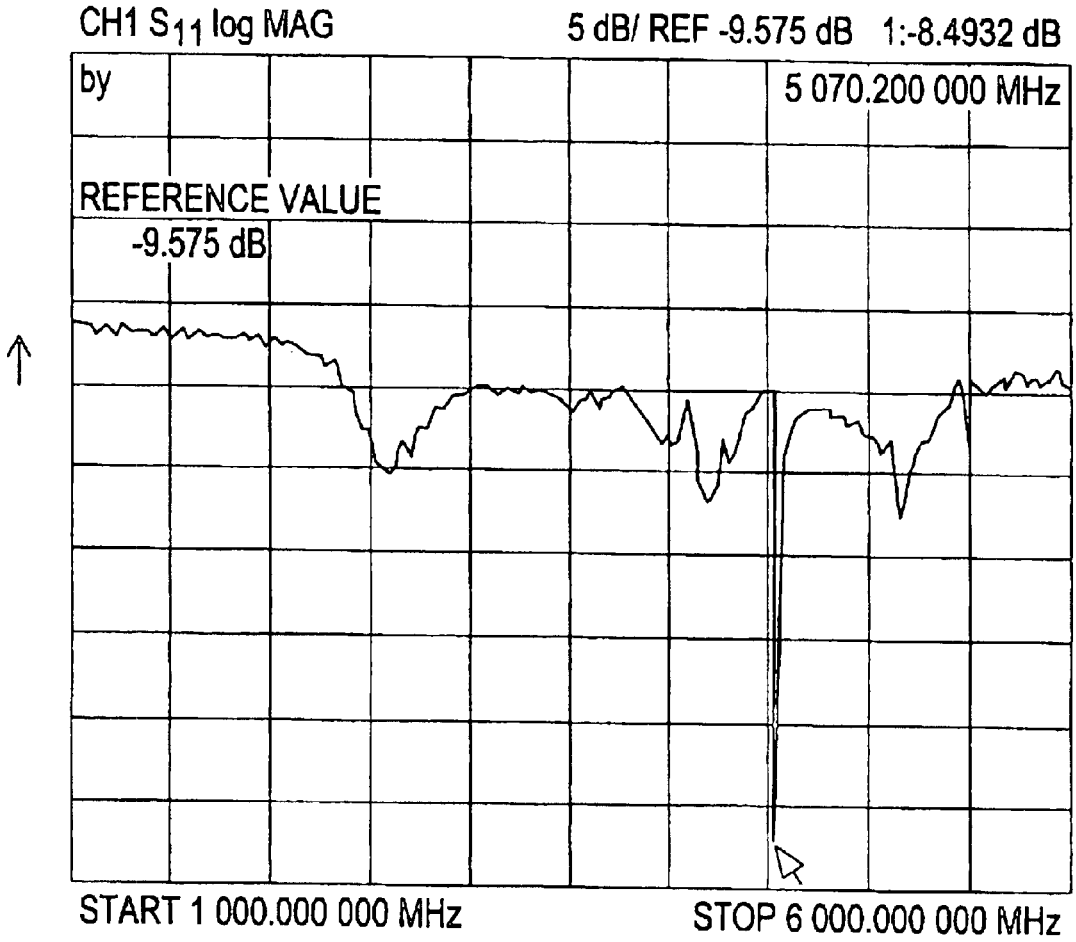
FIG. 12(A) is a diagram showing a reflection energy spectrum in blank measurement in the embodiment of FIG. 11.
Figure 12B:
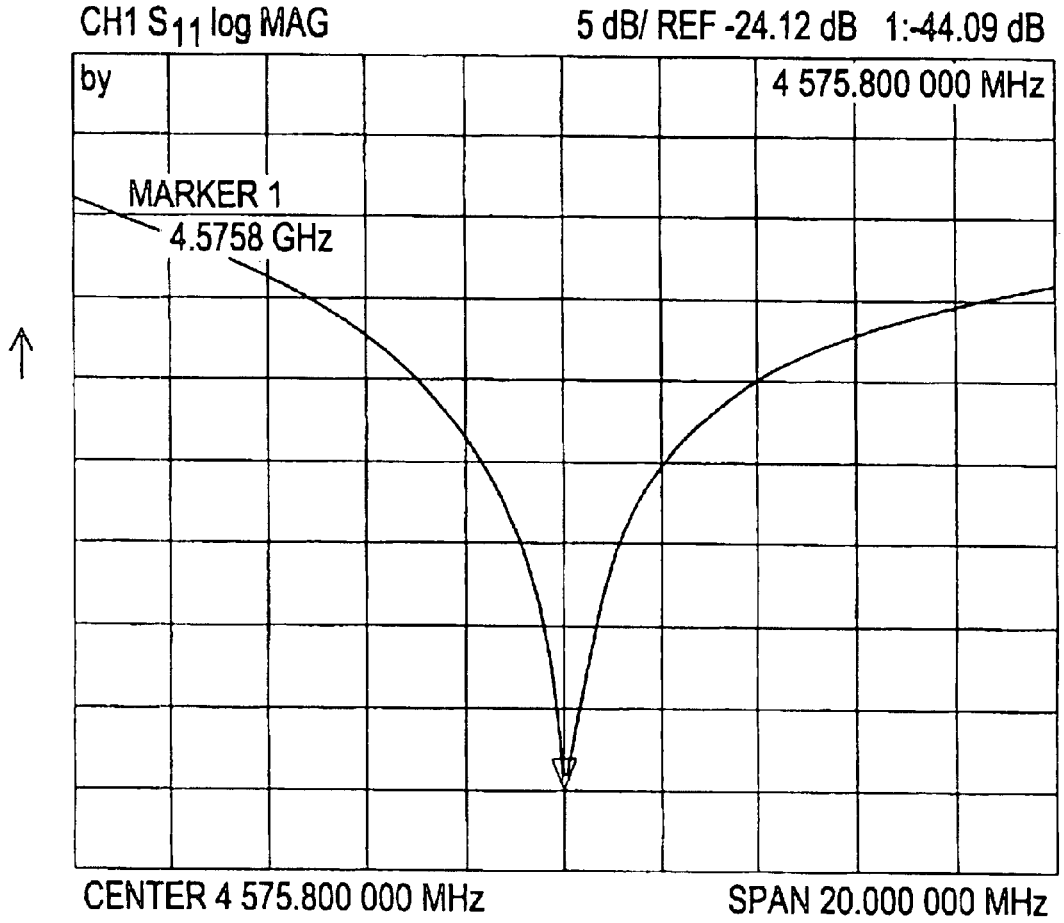
FIG. 12(B) is a diagram showing a peak thereof shown by arrow.

FIG. 12 shows a measurement result of the reflection energy in the embodiment of FIG. 11, and is an example of blank measurement in the case of placing no sample. (A)

shows a reflection energy spectrum when scanning microwave frequencies from 1000 MHz to 6000 MHz, and (B) is an enlargement of the area shown by arrow in (A), expressing a resonating state. Absorption of energy occurs on the position of a resonance frequency in the case of the reflection spectrum, and an absorption peak shown at (B) is obtained.

Figure 13A:
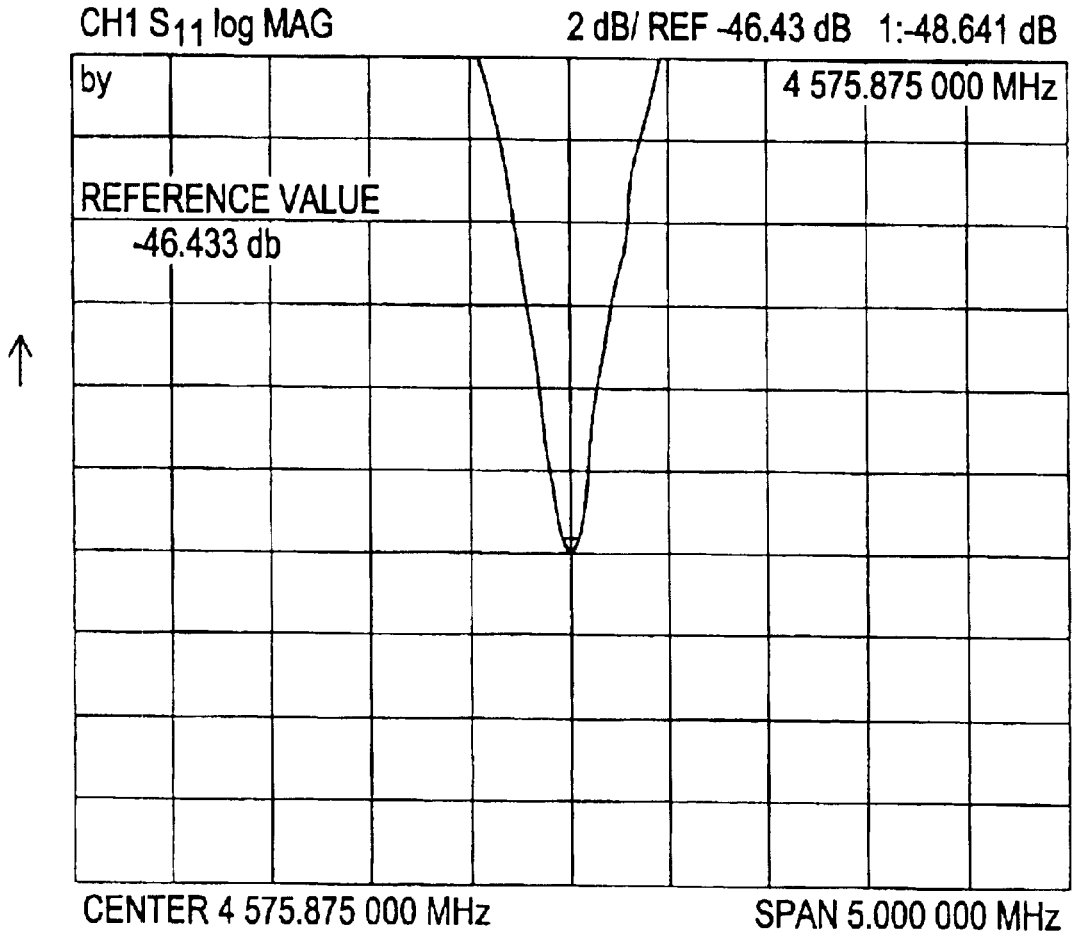
FIG. 13 illustrates diagrams showing peaks around 4575.875 MHz in the embodiment of FIG. 11, (A) is in blank measurement, and (B) is a case of placing paper as the sample.
Figure 13B:
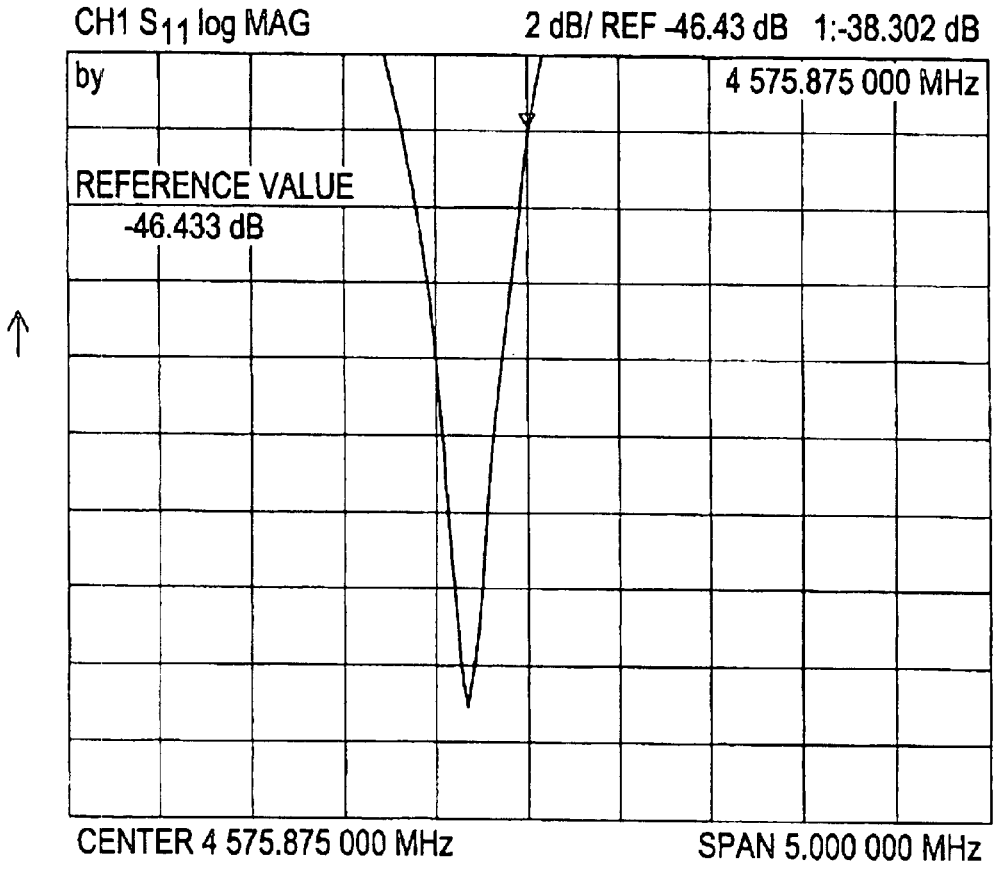

FIG. 13(A) shows a peak having the minimal point at 4575.875 MHz in blank measurement in the embodiment of FIG. 11. On the other hand, when placing a sheet of paper on the opening part of the shield case 35 as the sample, the minimal position of the peak shifts toward a lower frequency side as shown in (B). Supposing that measurement is performed at the frequency of 4575.875 MHz, it is understood that the output lowers by placing the sample. Also in this case, orientation can be measured as shown from FIG. 5 to FIG. 7 by rotating the sample or the dielectric resonator 20 in the plane parallel to the plane of the dielectric resonator 20, if the sample has anisotropy of the dielectric constant.

Figure 14:
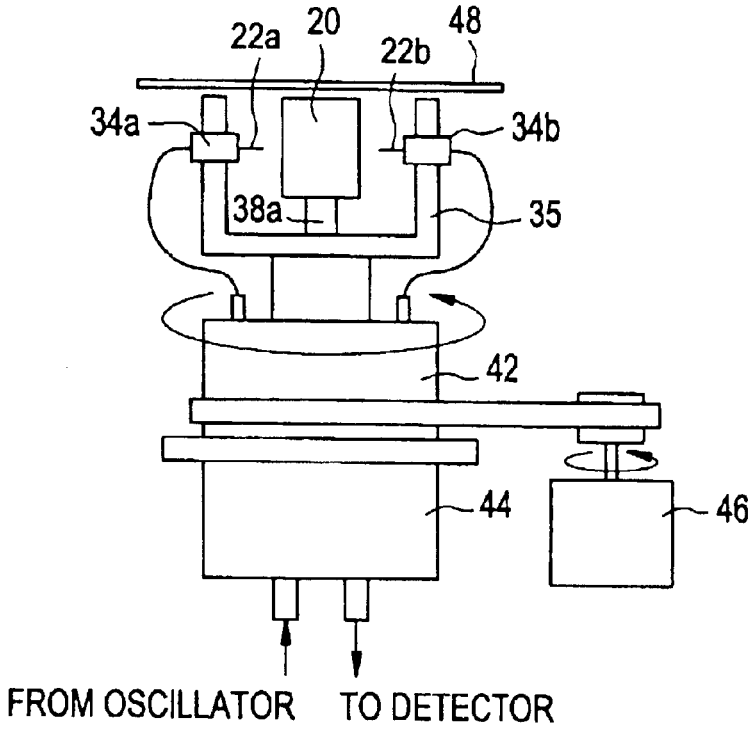
FIG. 14 is a front sectional view showing an embodiment rotating a dielectric resonator.

FIG. 14 shows a concrete example rotating a dielectric resonator 20. The dielectric resonator 20 and a shield case 35 are mounted on a rotary joint 42, to be rotated by a motor 46. Connectors 34a and 34b are connected to an oscillator and a detector by a joint 44 through the rotary joint 42 respectively. A sample 48 is arranged in approximation to the upper surfaces of the shield case 35 and the dielectric resonator 20.

In this case, transmission energy in each direction in the plane of the sample 48 is measured by rotating the dielectric resonator 20 and the shield case 35, and dielectric orientation of the sample 48 is obtained from the anisotropy thereof.

The sample 48 may be sequentially placed, or may be continuously moving. Online measurement is enabled when the sample 48 is continuously moving.

Figure 15:
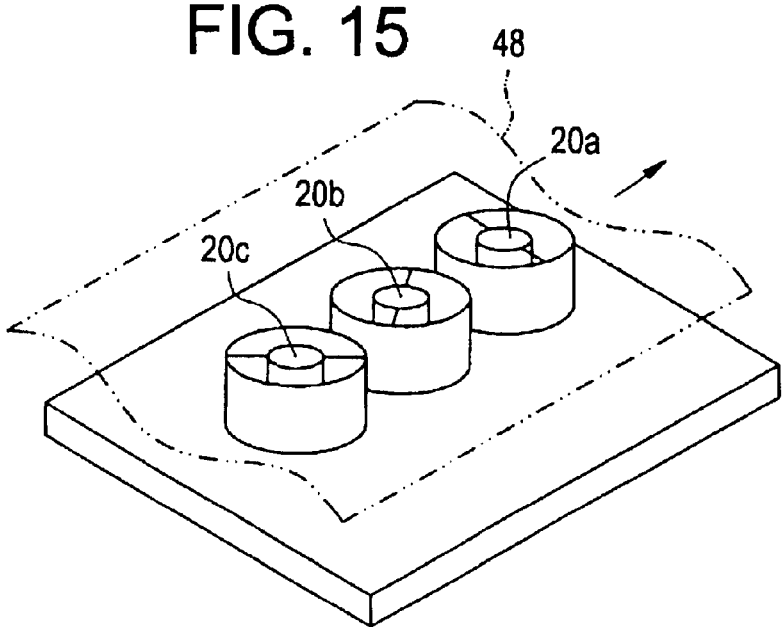
FIG. 15 is a schematic perspective view showing an embodiment having a plurality of dielectric resonators so set that directions of generated electric field vectors are different.
Figure 16A:
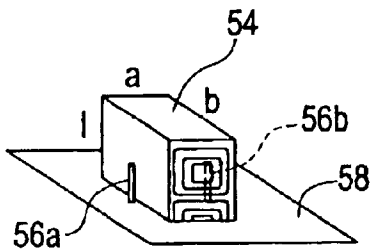
FIG. 16(A) is a schematic perspective view showing an embodiment combining a square resonator and a rod antenna.
Figure 16B:
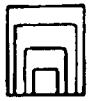
FIG. 16(B) is a chart showing resonance modes and resonance frequencies in the embodiment
Figure 16B:
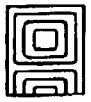
Figure 16B:
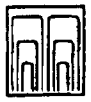
Figure 16B:
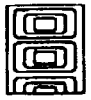
Figure 16B:
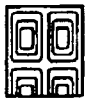

FIG. 15 schematically shows another embodiment for obtaining anisotropy, which does not rotate a dielectric resonator 20 as well as a sample 48 but arranges a plurality of dielectric resonators 20a, 20b and 20c so arranged that the directions of electric field vectors generated from the dielectric resonators are different in one plane so that the sample 48 moves on these dielectric resonators. Referring to FIG. 15, microwave transmission energy in directions different by 120° from each other is detected by three dielectric resonators 20a, 20b and 20c, and dielectric orientation of the sample is obtained.

The embodiment of FIG. 15 rotates neither the dielectric resonator 20 nor the sample 48, and hence can quickly obtain the dielectric orientation of the sample. When arranging the dielectric resonators 20a, 20b and 20c in a line along the travelling direction (direction of arrow) of the sample 48 as shown in FIG. 15 and synchronizing the timing of detection of the respective dielectric resonators 20a, 20b and 20c and the moving speed of the sample 48, the same place can be measured.

When arranging the dielectric resonators 20a, 20b and 20c in a direction perpendicular to the travelling direction of the sample 48, it follows that portions different from each other are measured, while the problem resulting from the difference of the measured places can be suppressed by arranging the same in approximation to each other.

Also when detecting the reflection energy as the embodiment of FIG. 11, the dielectric resonator can be rotated as shown in FIG. 14 or a plurality of dielectric resonators can be arranged while making the directions of electric field vectors different as shown in FIG. 15.

It has been recognized that, when employing a square resonator whose sample measuring surface is square or rectangular as the dielectric resonator, linear bar-like rod antennas are superior to loop antennas in uniformity of directions of electric field vectors in a measured in-sample plane as terminals of a microwave exciter and a detector. This is described with reference to FIG. 16 to FIG. 20.

FIG. 16 shows electrolytic distribution and resonance frequencies in the case of applying rod antennas to a square resonator. Referring to (A), a rod antenna 56a of an exciter is arranged on one side through a square resonator 54 having a rectangular sample measuring surface and a rod antenna 56b of a detector is arranged on the opposite side thereof. The bottom surface of the square resonator 54 is arranged in contact with a shielding material 58 of a conductive material. "a" and "b" show the lengths of the shorter and longer sides of the sample measuring surface of the square resonator 54, and l shows the height Table in (B) of FIG. 16 shows the respective dimensions a, b and l, electric field vector diagrams in respective resonance modes in the square resonator 54, and calculated values and measured values of the resonance frequency. The unit of the resonance frequency is GHz. In the modes having measured values, the calculated values and the measured values of the resonance frequency substantially coincide and it indicates that the illustrated resonance modes are proper.

Figure 17B:
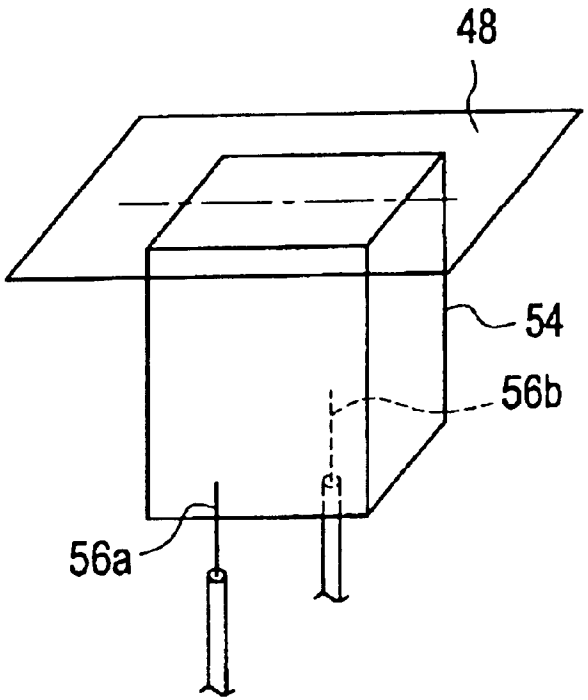
FIG. 17(B) is a schematic perspective view showing an embodiment combining a square resonator and a rod antenna.
Figure 17A:
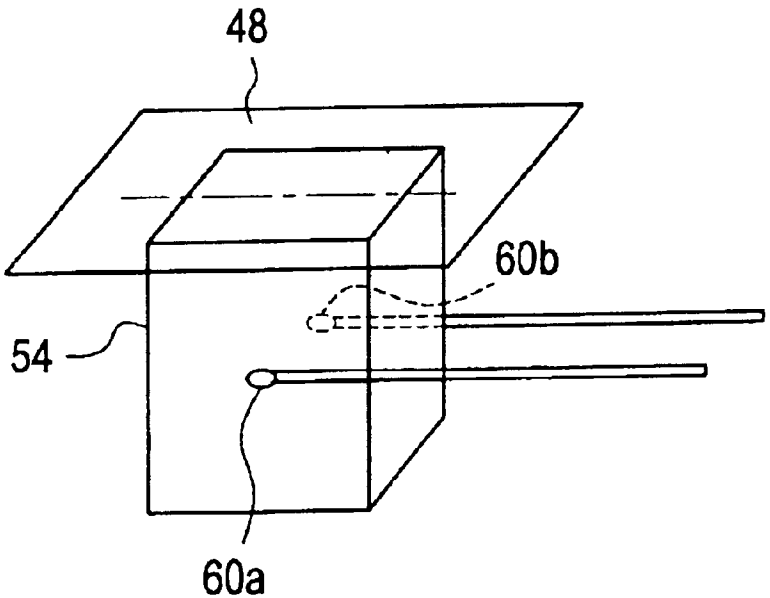
FIG. 17(A) is a schematic perspective view showing an embodiment combining a square resonator and a loop antenna.
Figure 18A:
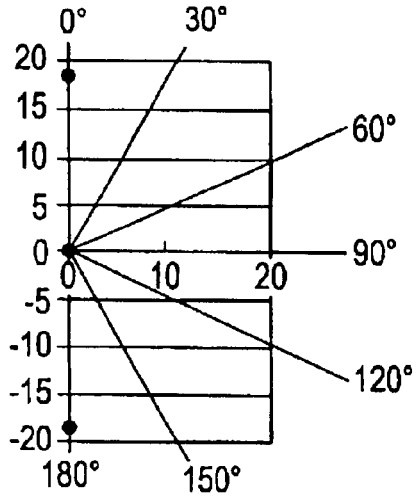
FIGS. 18(A) to (D) are diagrams showing electric field distribution in the case of employing a loop antenna or a rod antenna in a cavity resonator and a dielectric resonator respectively.
Figure 18B:
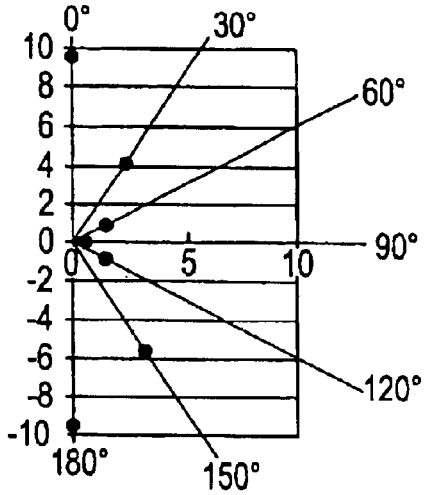
Figure 18C:
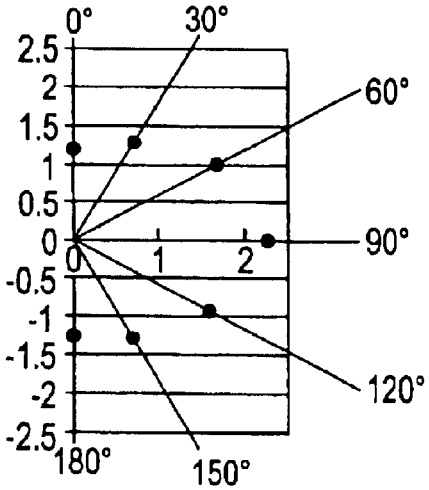
Figure 18D:
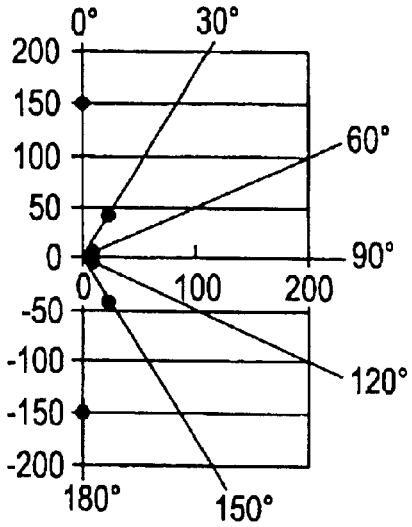
Figure 19A:
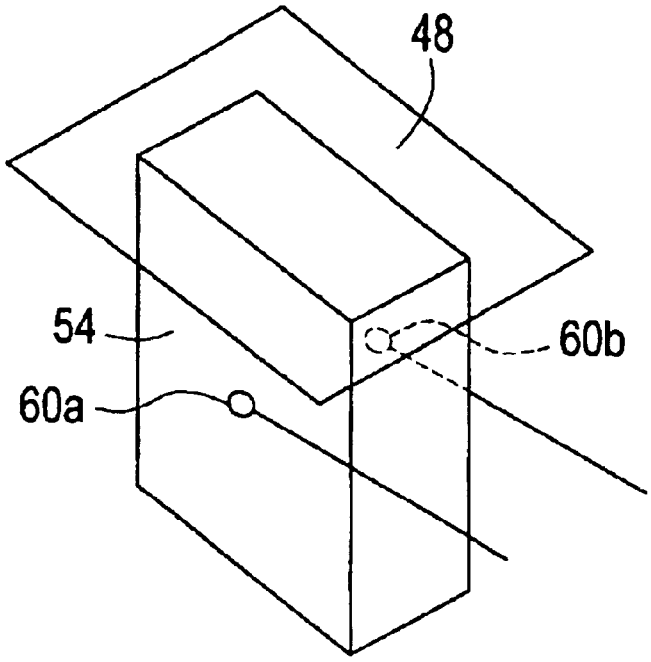
FIG. 19(A) is a schematic perspective view showing a measuring instrument combining a square resonator with a loop antenna, FIGS. 19(B) and (C) are plan views showing states of making measurement by rendering directions of the sample different by 90 degrees.
Figure 19B:
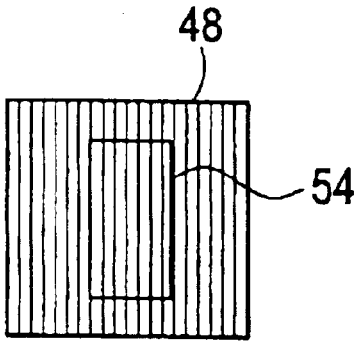
FIG. 19(D) is a diagram showing variation of a resonance spectrum with the direction of the sample.
Figure 19C:
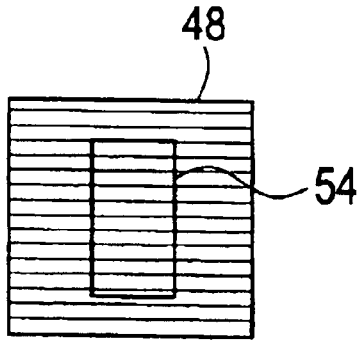
Figure 19D:
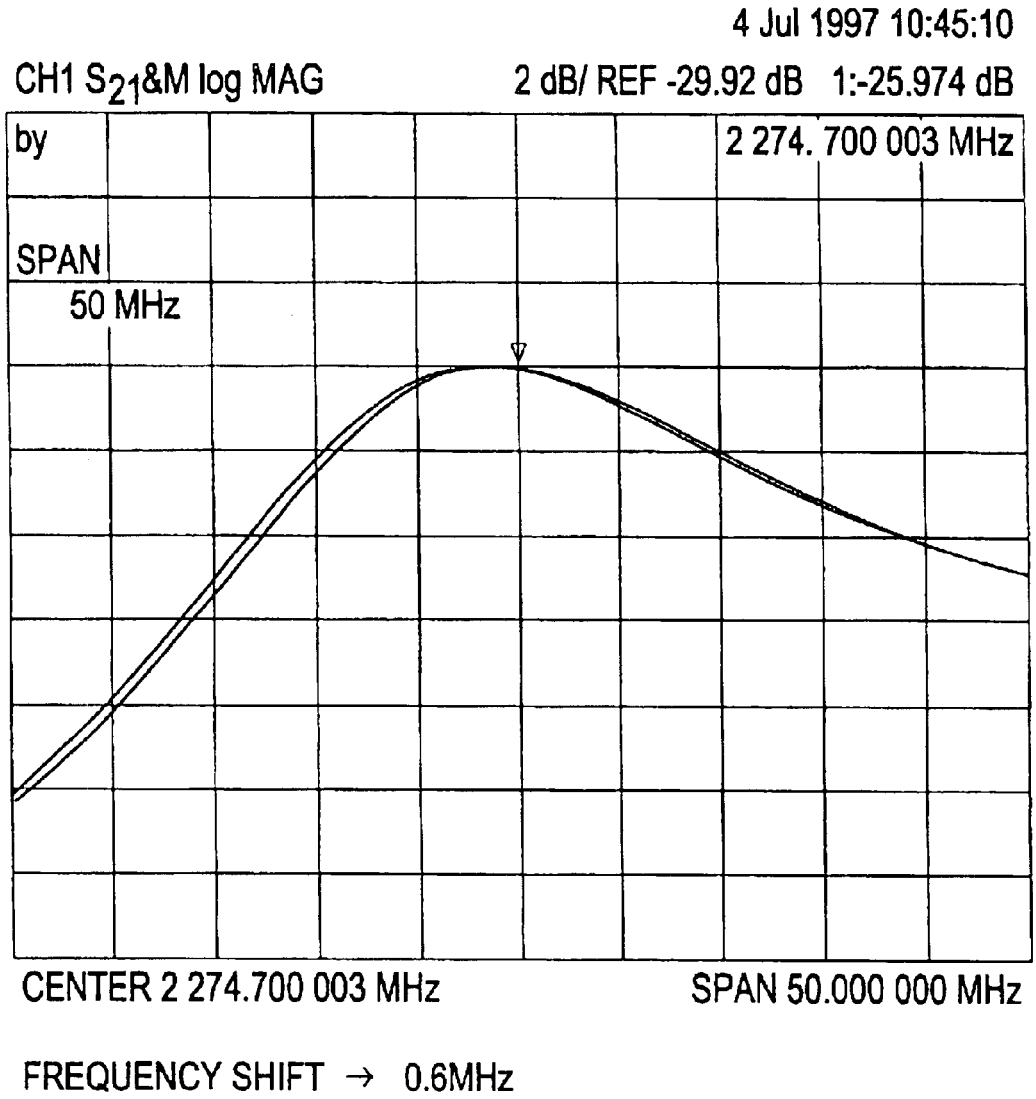

Next, distributions of electric field vectors of loop antennas and rod antennas are comparatively shown in the case of employing such a square resonator. FIG. 17(A) shows the case of employing loop antennas 60a and 60b, and FIG. 17(B) shows the case of employing rod antennas 56a and 56b. It is assumed that directions shown by one-dot chain lines in planes where samples 48 are arranged are 0 degrees.

FIG. 18 shows results of comparing electric field distribution in the case of employing loop antennas or rod antennas in a cavity resonator and dielectric resonators. In the case of the square resonators, it was assumed that the directions of the one-dot chain lines were 0 degrees as shown in FIG. 17, and long and narrow papers (50 mm by 1.5 mm) impregnated with a wave absorber were placed on the sample measuring surfaces of the square resonators while changing the angle every 30 degrees, for measuring resonance peak levels. In the case of the cavity resonator, the long and narrow paper impregnated with the wave absorber was arranged in a clearance part where a sample was arranged while changing the angle every 30 degrees. While terminals of a microwave exciter and a detector were rod antennas at that time, the horizontal direction was assumed to be 0 degrees assuming that the antennas were arranged in a vertical direction.

In the case of the cavity resonator, resonance peaks are obtained only when arranging the long and narrow paper impregnated with the wave absorber in a direction of 0 degrees and a direction of 180 degrees, as shown in (A). It is understood from this that uniformity of the electric field vector direction is considerate in the cavity resonator.

(B) shows the case of combining a circular dielectric resonator with loop antennas, and indicates that an electric field vector other than a unidirectional component is also present (C) shows the case of combining a square dielectric resonator with loop antennas, and indicates that electric fields are directed to respective directions in this case and uniformity is inferior.

Figure 20A:
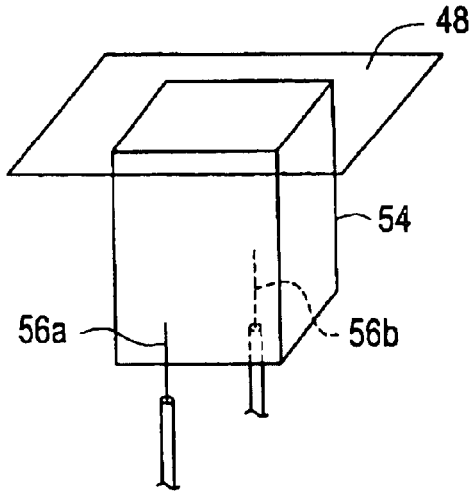
FIG. 20(A) is a schematic perspective view showing a measuring instrument combining a square resonator with a rod antenna.

(D) shows the case of combining a square dielectric resonator with rod antennas, and indicates that it has electric fields having superior uniformity to the case (B) of employing loop antennas although electric field vectors other than a unidirectional component are also present FIG. 19 and FIG. 20 show results of measuring a sample with such a dielectric resonator. As shown in FIG. 19(A), glass fiber was employed as a sample 48 in a measuring instrument combining a square dielectric resonator 54 with loop antennas 60a and 60b and its direction was made to differ by 90 degrees as shown in (B) and (C) in FIG. 19 for measuring resonance. Consequently, although frequency shifting is observed as shown in FIG. 19(D), the shift quantity is small at approximately 0.6 MHz.

Figure 20B:
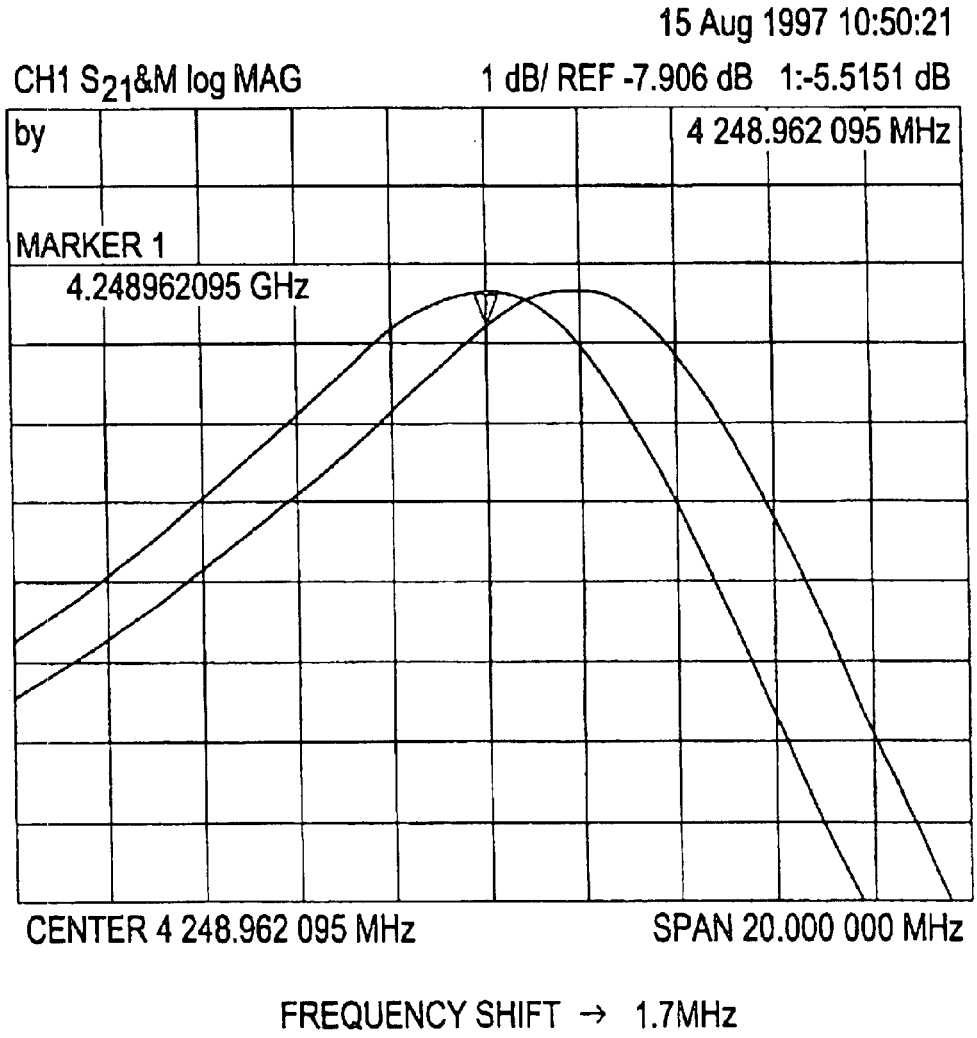
FIG. 20(B) is a diagram showing variance of a resonance spectrum depending on the direction of a sample.

On the other hand, in FIG. 20, a square dielectric resonator 54 was combined with rod antennas 56a and 56b as shown in (A), and glass fiber was similarly employed as a sample 48 and measurement was made while making the direction different by 90 degrees. Consequently, resonance frequency shifting was large and reached 1.7 MHz as shown in FIG. 20(B), and it indicates that measurement of higher sensitivity can be made.

Figure 21A:
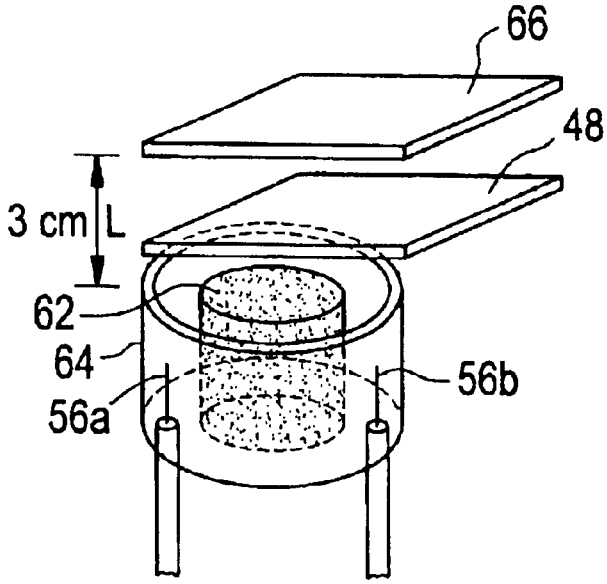
FIG. 21(A) is a schematic perspective view showing an embodiment comprising a shielding member.
Figure 21B:
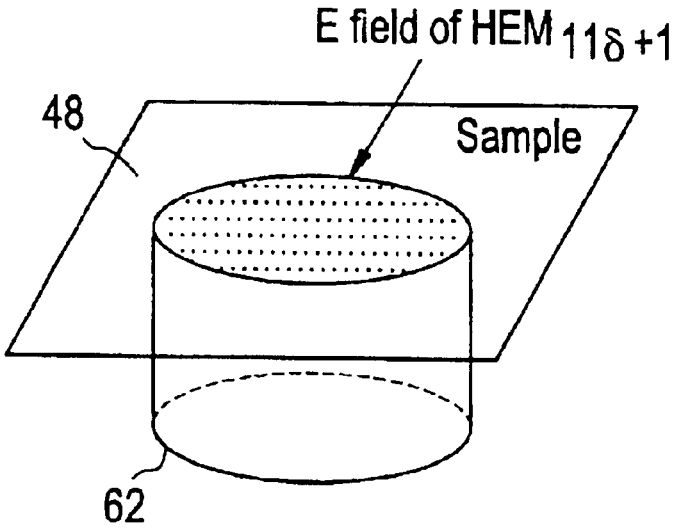
FIG. 21(B) is a schematic perspective view showing an electric field vector of a dielectric resonator of this embodiment.

FIG. 21 shows an embodiment having a shielding member. As shown in (A), a circular dielectric resonator 62 is stored in a shield case 64 formed by a cylindrical container of brass, the bottom surface of the dielectric resonator 62 is in contact with the shield case 64, and the upper surface of the dielectric resonator 62 and an opening part of the shield case 64 are set flush with each other. A rod antenna 56a of an exciter and a rod antenna 56b of a detector are arranged between the side surface of the dielectric resonator 62 and the inner wall surface of the shield case 64 in positions opposed through the dielectric resonator 62. A sample 48 is arranged to be close to the upper surface of the dielectric resonator 62. A shielding member 66 of brass is arranged above a surface of the sample 48 opposite to the dielectric resonator 62.

While Q at the resonance frequency of this dielectric resonator was 900 when arranging no shielding member 66, Q increased to 1700 when arranging the shielding member 66 on a position separated from the opening end of the shielding case 64 by a distance L of 30 mm.

FIG. 21 (B) shows an electric field vector of the dielectric resonator 62 of this embodiment, and the mode is $HEM_{11\delta+1}$. The electric field includes a unidirectional component on a sample measuring surface.

Figure 22:
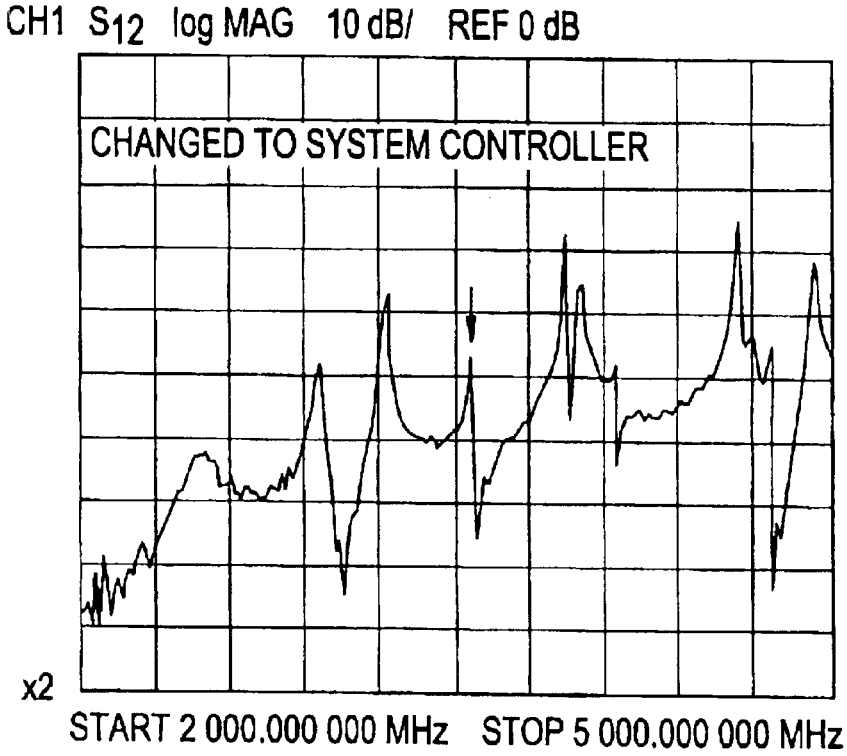
FIG. 22 is a diagram showing a resonance spectrum measuring a PET sample with the embodiment of FIG. 21.
Figure 23:
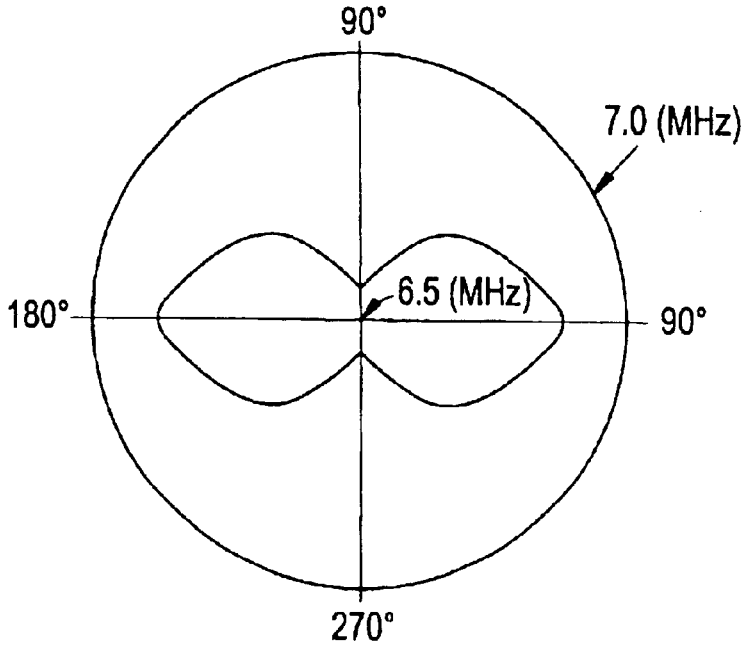
FIG. 23 is a diagram showing variance of a resonance frequency when rotating a sample in a plane in the embodiment of FIG. 21.

FIG. 22 shows a resonance spectrum obtained by measuring a sheet-like sample of 192 μm in thickness of biaxially oriented (bi: axialy oriented) PET (polyethylene terephthalate) with the dielectric resonator (that having the shielding member 66) of this embodiment FIG. 23 shows variance of the resonance frequency when rotating the sample in a plane as to a peak in the resonance spectrum shown by arrow. FIG. 23 shows, with reference to the resonance frequency in blank measurement when placing no sample, frequency variance therefrom with respect to a rotational angle. The coordinates in the radial direction are set at 6.5 MHz at the center, and at 7.0 MHz on the periphery. From this result, it can be clearly read that the PET sheet comprises dielectric anisotropy in the plane.

Figure 24:
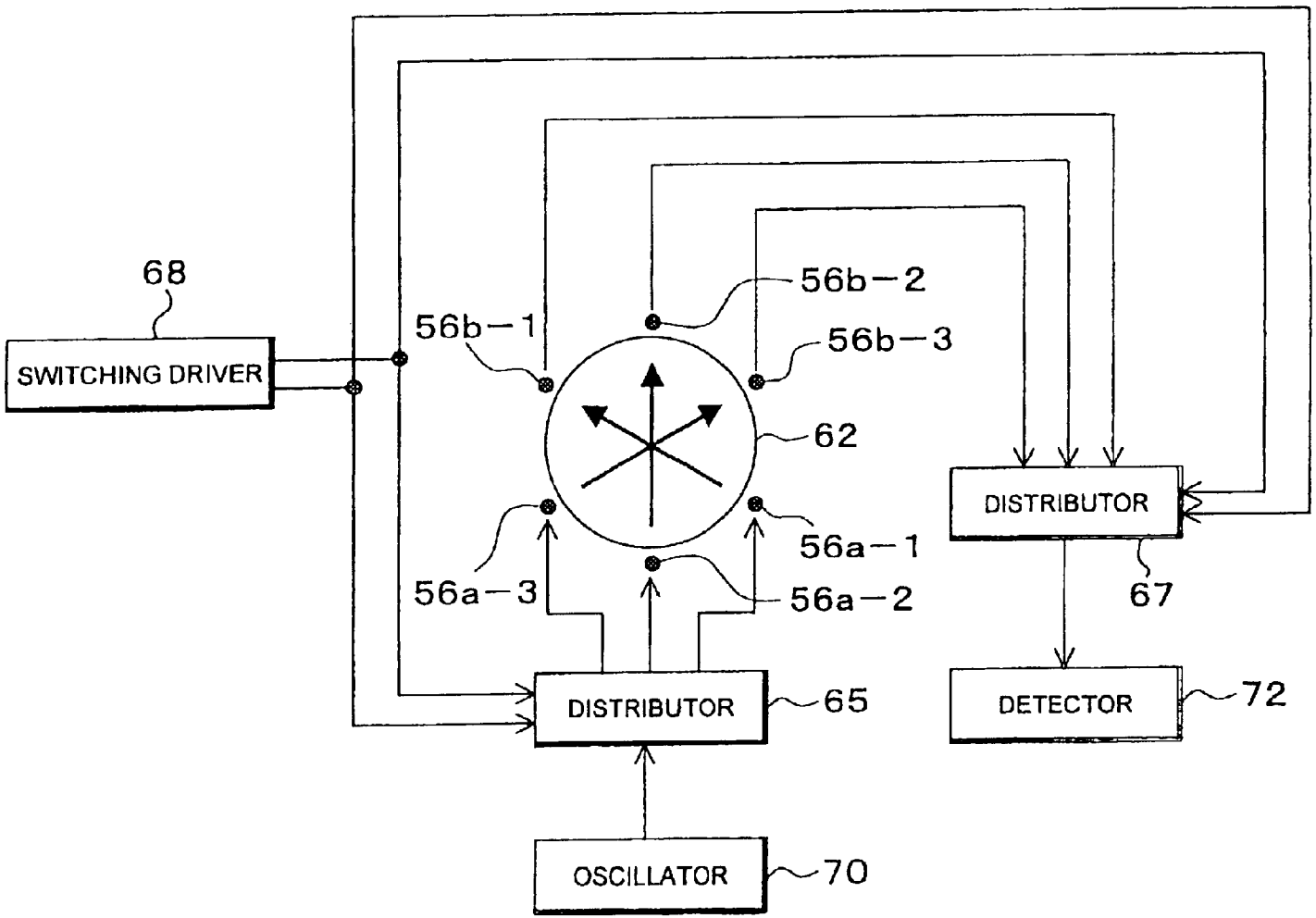
FIG. 24 is a schematic block diagram showing another embodiment measuring dielectric resonance of a sample while rotating neither a dielectric resonator nor the sample.

FIG. 24 shows another embodiment measuring dielectric anisotropy of a sample while rotating neither a dielectric resonator nor a sample. Three pairs of rod antennas are arranged around a circular dielectric resonator 62. 56a-1, 56a-2 and 56a-3 are rod antennas of an exciter, and 56b-1, 56b-2 and 56b-3 are rod antennas of a detector. The rod antennas 56a-1 and 56b-1 are arranged to hold the resonator 62 in a pair, 56a-2 and 56b-2 are arranged to hold the resonator 62 in a pair, and 56a-3 and 56b-3 are arranged to hold the resonator 62 in a pair. Each rod antenna is so arranged that the direction of an electric field vector generated by the rod antenna 56a-1 and the direction of an electric field vector generated by the rod antenna 56a-2 form 60 degrees, and the direction of an electric field vector generated by the rod antenna 56a-2 and the direction of an electric field vector generated by the rod antenna 56a-3 further form 60 degrees. 70 is an oscillator of the exciter, and connection between the oscillator 70 and the rod antennas 56a-1 to 56a-3 is successively switched by a distributor 65. 72 is a detector, and connection between the detector 72 and the rod antennas 56b-1 to 56b-3 is successively switched by a distributor 67. The distributors 65 and 67 are synchronously controlled by a switching driver 68 to make each pair of rod antennas connected to the oscillator 70 and the detector 72 respectively.

In the embodiment of FIG. 24, resonance spectra of three directions different by 60 degrees can be measured when a sample is present on a sample measuring surface of the resonator 62 by switching operating rod antenna pairs by the switching driver 68, and dielectric anisotropy in a sample plane can be measured while rotating neither the sample nor the resonator 62.

While the sample measuring surface of the resonator 62 is circular in the embodiment of FIG. 24, uniformity of electric field vectors is improved when the sample measuring surface is rather polygonal than circular in the case of employing rod antennas as the terminals of the oscillator and the detector. Therefore, the shape of the sample measuring surface of the resonator 62 can be rendered orthohexagonal in the embodiment of FIG. 24.

Figure 25:
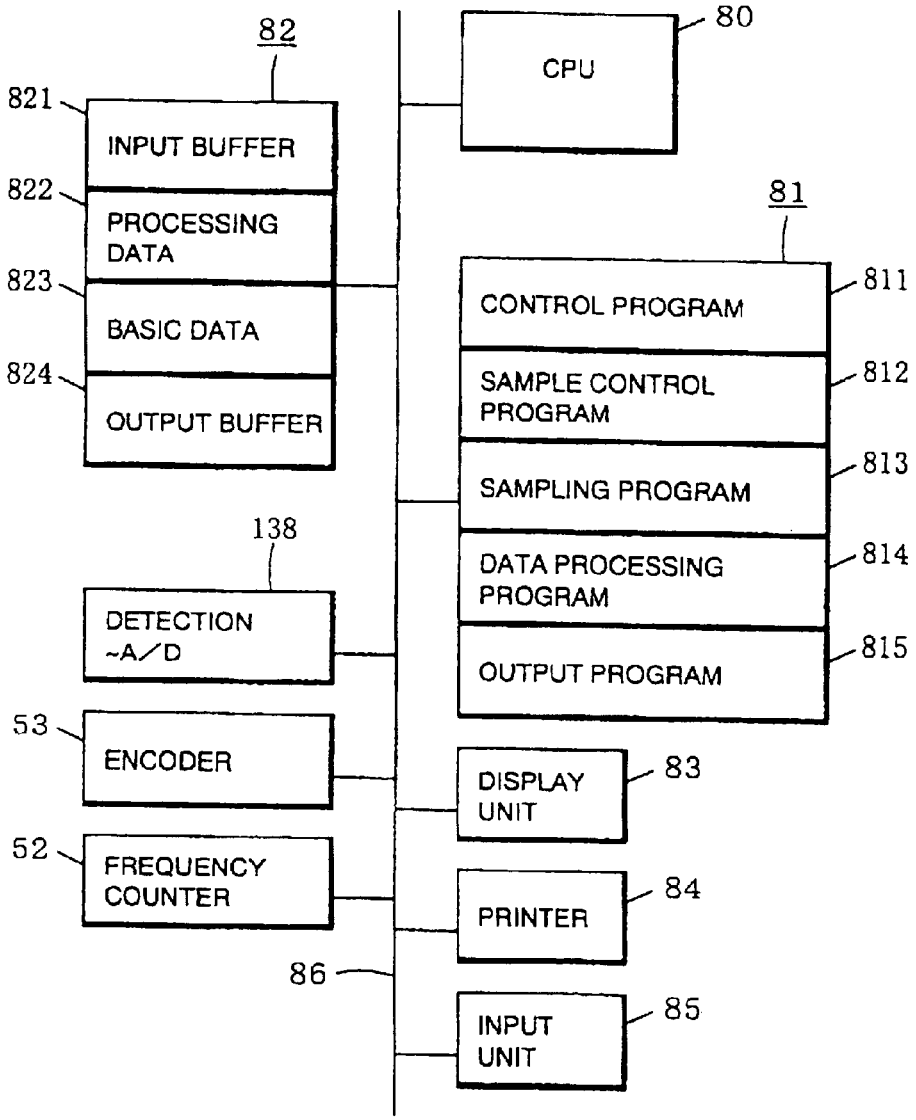
FIG. 25 is a block diagram schematically showing a computer as a data processor.

FIG. 25 schematically shows a computer as a data processor processing microwave detection output data converted to a digital signal by an A–D converter and captured. 80 is a CPU, 81 is a control part, 82 is a data storage memory, 83 is a display unit such as a CRT or a liquid crystal panel, 84 is a printer, and 85 is an input unit such as a keyboard and others.

In the control part 81, a control program storage part 811 includes a microwave power supply program and others in addition to a program controlling operations of the overall device. A sample control program storage part 812, for example, stores a program controlling the operation of rotating the sample or the dielectric resonator in the embodiment of FIG. 14, or the operation of switching the operating rod antenna pairs in the embodiment of FIG. 24. A sampling program storage part 813 stores a sampling program for detection data, and the sampling program controls the timing of detection data sampling and the timing of A–D conversion by the A–D converter 138. A data processing program stored in a data processing program storage part 814 controls processing such as storage, arithmetic processing and others of measurement data (including data such as transmission or reflection microwave intensity detection data and a measured microwave frequency corresponding thereto, a use number, a rotational angle of a sample and the like) sampled and introduced into this data processor, and performs formation of an orientation pattern from the measurement data and operation induction of the orientation direction and the degree of orientation.

An output program stored in an output program storage part 815 controls an operation of selecting the orientation pattern, the orientation direction, the degree of orientation and the like at any time and outputting the same to the display unit 83 or the printer 84.

The data storage memory 82 comprises an input buffer memory area 821 for temporarily storing the measurement data introduced into this data processor, a processing data area 822 storing processing data calculating the orientation direction, the degree of orientation, the orientation pattern and others from these data, a storage area 823 of basic data for data processing, an output buffer memory area 824 storing or updating displayed or printed data at any time and the like.

A rotary encoder 53 is provided for detecting the rotational angle of a sample or a dielectric resonator. 52 is a frequency counter, which is provided on, for example, a microwave oscillator. A rotational angle signal of the sample by the rotary encoder 53 and a measured frequency signal by the frequency counter 52 are introduced into this data processor in correspondence to sample transmission or reflection microwave intensity detection data by the A–D converter.

What is claimed is:

1. An orientation measuring instrument comprising:

a dielectric resonator having a plane being *close to or* in contact with a sample, [sample] *said* dielectric resonator arranged [on] *less than 3 cm from* a first surface of the sample;

a microwave exciter generating an electric field vector having a unidirectional component at a frequency in the vicinity of the resonance frequency of said dielectric resonator when the sample is present and in an in-sample plane parallel to said plane in said dielectric resonator;

a detector detecting transmission energy or reflection energy by said dielectric resonator;

a rotation mechanism rotating said sample or said dielectric resonator in a plane parallel to said plane; and a data processor obtaining dielectric anisotropy of the sample from variance of a detection output of said detector following rotation by the rotation mechanism whereby said orientation measuring instrument measures orientation of a portion of the sample,

*wherein said dielectric resonator is a square resonator,*

*terminals of said exciter and said detector are bar-like rod antennas having been arranged in a direction perpendicular to the plane of said dielectric resonator being close to or being in contact with the sample, and*

*the periphery of said dielectric resonator is covered with a shielding material consisting of a conductive material except a sample measuring surface.*

2. An orientation measuring instrument comprising:

a plurality of dielectric resonators comprising planes being *close to or* in contact with a sample and arranged close to each other, said dielectric resonators arranged [in] *less than 3 cm from* a first surface of the sample;

[a] microwave exciter*s* generating electric field vectors having unidirectional components, being electric filed vectors having directions different from each other at a frequency in the vicinity of the resonance frequency of said dielectric resonator when the sample is present and in an in-sample plane parallel to said planes in the respective dielectric resonators;

detectors for the respective dielectric resonators detecting transmission energy or reflection energy by these dielectric resonators; and a data processor obtaining dielectric anisotropy of the sample from variance of detection outputs by said detectors at said electric field vectors of different directions from said plurality of dielectric resonators whereby said orientation measuring instrument measures orientation of a portion of the sample,

*wherein said dielectric resonators is a square resonator,*

*terminals of said exciters and said detectors are bar-like rod antennas having been arranged in a direction perpendicular to the planes of said dielectric resonator(s) being close to or being in contact with the sample, and*

*the periphery of said dielectric resonators is covered with a shielding material consisting of a conductive material except a sample measuring surface.*

[3. An orientation measuring instrument comprising:

a dielectric resonator having a plane being in contact with a sample, said dielectric resonator arranged on a first surface of the sample;

a plurality of sets, being sets of microwave exciters generating electric filed vectors having unidirectional components at a frequency in the vicinity of the resonance frequency of said dielectric resonator when the sample if present and in an in-sample plane parallel to said plane in said dielectric resonator and detectors detecting transmission energy or reflection energy by said dielectric resonator, arranged on positions different from each other with respect to said dielectric resonator;

a switching driver selecting one set among said plurality of sets of microwave exciters and detectors and sequentially driving the same; and a data processor obtaining dielectric anisotropy of the sample from variance of detection outputs of said detectors following switching by said switching driver whereby said orientation measuring instrument measures orientation of a portion of the sample.]

4. The orientation measuring instrument in accordance with [any of claims 1 to 3,] *claim 1 or 2,* employing variance of the resonance frequency as variance of said detection output(s).

5. The orientation measuring instrument in accordance with claim 1 [2 or 3,] *or 2,* employing variance of detection energy at a specific frequency as variance of said detection output(s).

6. The orientation measuring instrument in accordance with claim 1 [2 or 3,] *or 2,* wherein said exciter(s) and said detector(s) comprise a terminal pair oppositely arranged through the dielectric resonator(s) for detecting transmission energy by said detector(s).

7. The orientation measuring instrument in accordance with claim 1 [2 or 3,] *or 2,* wherein said exciter(s) and said detector(s) comprise a common terminal arranged closely to the dielectric resonator(s) for detecting reflection energy by said detector(s).

[8. The orientation measuring instrument in accordance with claim 1, 2 or 3, wherein said dielectric resonator(s) is a cylindrical resonator.]

[9. The orientation measuring instrument in accordance with claim 1, 2 or 3, wherein said dielectric resonator(s) is a square resonator.]

[10. The orientation measuring instrument in accordance with claim 1, 2 or 3, wherein terminals of said exciter(s) and said detector(s) are bar-like rod antennas having been arranged in a direction perpendicular to the plane(s) of said dielectric resonator(s) being close to or being in contact with the sample.]

[11. The orientation measuring instrument in accordance with claim 1, 2 or 3, wherein the periphery of said dielectric resonator(s) is covered with a shielding material consisting of a conductive material except a sample measuring surface.]

12. The orientation measuring instrument in accordance with claim [11,] *1 or 2,* wherein a*nother* shielding material consisting of a conductive material is arranged also on a sample measuring surface side of said dielectric resonator(s), and the sample is arranged between the sample measuring surface of the dielectric resonator(s) and said shielding material on the sample measuring surface side.

* * * * *